(12) United States Patent
Fischmeister et al.

(10) Patent No.: US 6,506,580 B1
(45) Date of Patent: Jan. 14, 2003

(54) SPLICE VARIANTS FOR HUMAN 5-HT$_4$ SEROTONIN RECEPTOR AND THEIR APPLICATIONS, IN PARTICULAR FOR SCREENING

(75) Inventors: Rodolphe Fischmeister, Orsay (FR); Michel Langlois, Sceaux (FR); Yamina Dahmoune, Joinville le Pont (FR); Monique Gastineau, Wissous (FR); Olivier Blondel, Washington, DC (US); Johan Hoebeke, Schtiltigheim (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 09/555,313

(22) PCT Filed: Nov. 27, 1998

(86) PCT No.: PCT/FR98/02560

§ 371 (c)(1),
(2), (4) Date: Sep. 19, 2000

(87) PCT Pub. No.: WO99/28456

PCT Pub. Date: Jun. 10, 1999

(30) Foreign Application Priority Data

Nov. 28, 1997 (FR) ............................................ 97 15037

(51) Int. Cl.$^7$ ........................ C12N 15/12; G01N 33/567
(52) U.S. Cl. ................ 435/69.1; 435/252.3; 435/320.1; 435/7.1; 435/7.2; 435/7.21
(58) Field of Search ............................ 435/69.1, 252.3, 435/320.1, 7.1, 7.2, 7.21; 536/23.5

(56) References Cited

U.S. PATENT DOCUMENTS 5,472,866 A * 12/1995 Gerald et al. ................ 435/240
5,766,879 A *  6/1998 Gerald et al. .............. 435/69.1

FOREIGN PATENT DOCUMENTS

| EP | 0 683 161 A1 | 11/1995 |
| WO | WO 94/09828 | 5/1994 |
| WO | WO 94/14957 | 7/1994 |

OTHER PUBLICATIONS

Blondel et al., "Molecular and functional characterization of a 5–HT$_4$ receptor cloned from human atrium", FEBS Letters 412 (1997) 465–474.
Hoyer et al., "5–HT Receptor Classification and Nomenclature: Towards a Harmonization with the Human Genome", *Neuropharmacology*, vol. 36, No. 4/5, pp. 419–428, 1997.
Bond et al., "Romancing receptor search at Verona classification meeting", Trends in Pharmacological Sciences, vol. 17, No. 3, Mar. 1996, pp. 85–89.

* cited by examiner

*Primary Examiner*—John Ulm
(74) *Attorney, Agent, or Firm*—Larson & Taylor PLC

(57) ABSTRACT

The invention concerns an isolated polypeptide constitutive of splice variants for human serotonin receptor whereof the amino acid sequence is selected among the sequence SEQ ID No. 2 of the 5-HT$_{4(c)}$ polypeptide variant or the sequence SEQ ID No. 4 of the 5–HT$_{4(d)}$ polypeptide variant, or any polypeptide fragment or biologically active derivative thereof. The invention also concerns the inverse agonist effect of ML 10375 on 5-HT4(c) and 5-HT4(d) receptors.

Figure 3:
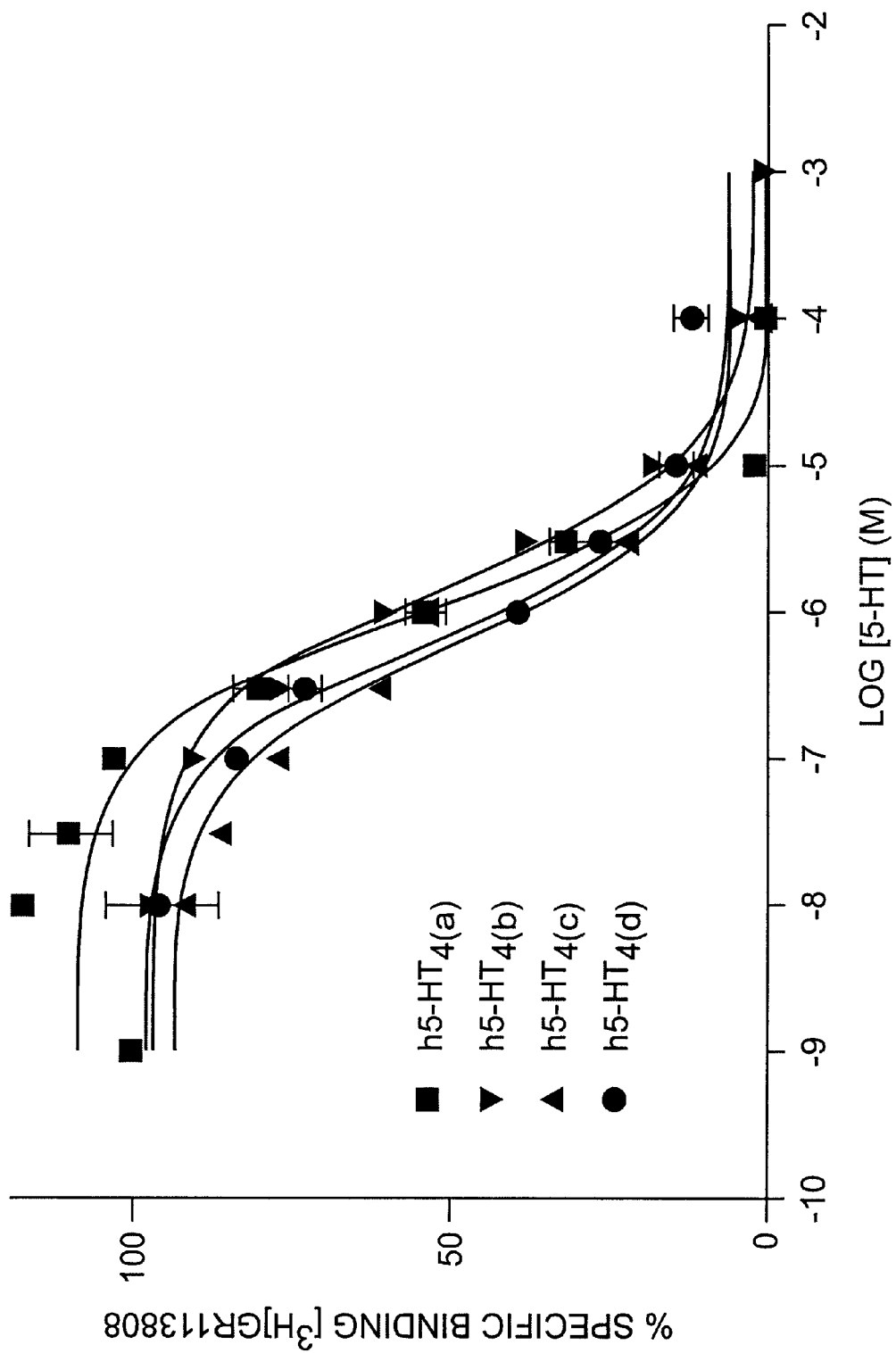

6 Claims, 16 Drawing Sheets h5-HT₄(a)  LRYTVLHRGHHQELEKLPIHNDPESLESCF*  387
r5-HT₄S    LRYTVLHSGQHQELEKLPIHNDPESLESCF*  387 h5-HT₄(b)  LRDAVECGGQWESQCHPPATSPLVAAQPSDT*           388
r5-HT₄L    LRDTVECGGQWESRCHLTATSPLVAAQPVIRRPQDNDLEDSCSLKRSQS*  406 h5-HT₄(c)  LSSGTETDRRNFGIRKRRLTKPS*  380 h5-HT₄(d)  LRF*  360

FIG. 1A

| | | |
|---|---|---|
| h5-HT₄(c) | MDKLDANVSSEEGFGSVEKVVLLTFLSTVILMAILGNLLVMVAVCWDRQL | 50 |
| h5-HT₄(d) | MDKLDANVSSEEGFGSVEKVVLLTFLSTVILMAILGNLLVMVAVCWDRQL | 50 |

TM1

| | | |
|---|---|---|
| h5-HT₄(c) | RKIKTNYFIVSLAFADLLVSVLVMPFGAIELVQDIWIYGEVFCLVRTSLD | 100 |
| h5-HT₄(d) | RKIKTNYFIVSLAFADLLVSVLVMPFGAIELVQDIWIYGEVFCLVRTSLD | 100 |

TM2

| | | |
|---|---|---|
| h5-HT₄(c) | VLLTTASIFHLCCISLDRYYAICCQPLVYRNKMTPLRIALMLGGCWVIPT | 150 |
| h5-HT₄(d) | VLLTTASIFHLCCISLDRYYAICCQPLVYRNKMTPLRIALMLGGCWVIPT | 150 |

TM3         TM4

| | | |
|---|---|---|
| h5-HT₄(c) | FISFLPIMQGWNNIGIIDLIEKRKFNQNSNSTYCVFMVNKPYAITCSVVA | 200 |
| h5-HT₄(d) | FISFLPIMQGWNNIGIIDLIEKRKFNQNSNSTYCVFMVNKPYAITCSVVA | 200 |

TM5

| | | |
|---|---|---|
| h5-HT₄(c) | FYIPFLLMVLAYYRIYVTAKEHAHQIQMLQRAGASSESRPQSADQHSTHR | 250 |
| h5-HT₄(d) | FYIPFLLMVLAYYRIYVTAKEHAHQIQMLQRAGASSESRPQSADQHSTHR | 250 |

| | | |
|---|---|---|
| h5-HT₄(c) | MRTETKAAKTLCIIMGCFCLCWAPFFVTNIVDPFIDYTVPGQVWTAFLWL | 300 |
| h5-HT₄(d) | MRTETKAAKTLCIIMGCFCLCWAPFFVTNIVDPFIDYTVPGQVWTAFLWL | 300 |

TM6

| | | |
|---|---|---|
| h5-HT₄(c) | GYINSGLNPFLYAFLNKSFRRAFLIILCCDDERYRRPSILGQTVPCSTTT | 350 |
| h5-HT₄(d) | GYINSGLNPFLYAFLNKSFRRAFLIILCCDDERYRRPSILGQTVPCSTTT | 350 |

TM7

| | | |
|---|---|---|
| h5-HT₄(c) | INGSTHVLSSGTETDRRNFGIRKRRLTKPS* | 380 |

| | | |
|---|---|---|
| h5-HT₄(d) | INGSTHVLRF* | 360 |

| | |
|---|---|
| TM | PUTATIVE TRANSMEMBRANE SEGMENT |
| ↑ | ALTERNATIVE SPLICING SITE |
| * | TERMINAL STOP CODON |
| ● | POTENTIAL N-GLYCOSYLATION SITE |
| △ | POTENTIAL PALMITOYLATION SITE |
| ○ | PROTEIN KINASE C PHOSPHORYLATION CONSENSUS SITE |
| † | CASEIN KINASE II PHOSPHORYLATION CONSENSUS SITE |
| ■ | cAMP/cGMP-DEPENDENT PROTEIN KINASE PHOSPHORYLATION CONSENSUS SITE |

*FIG. 1B*

FIG. 2

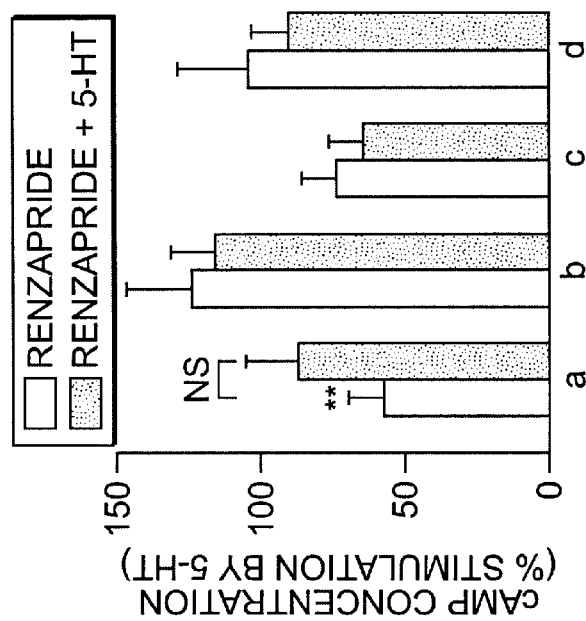
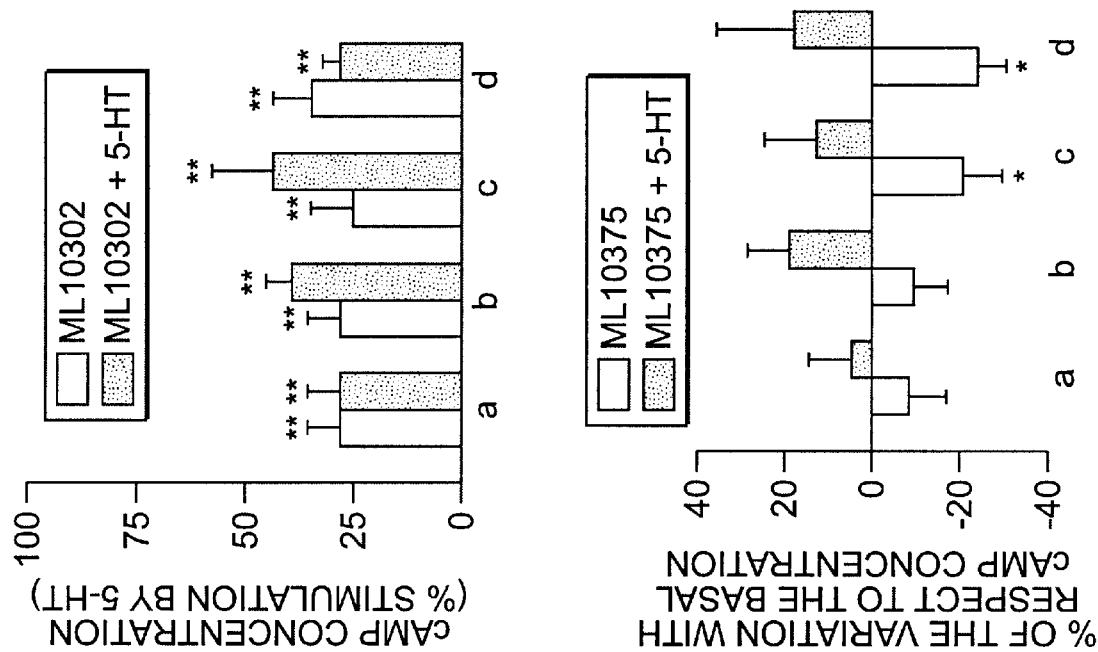
FIG. 5C
FIG. 5D
FIG. 5E

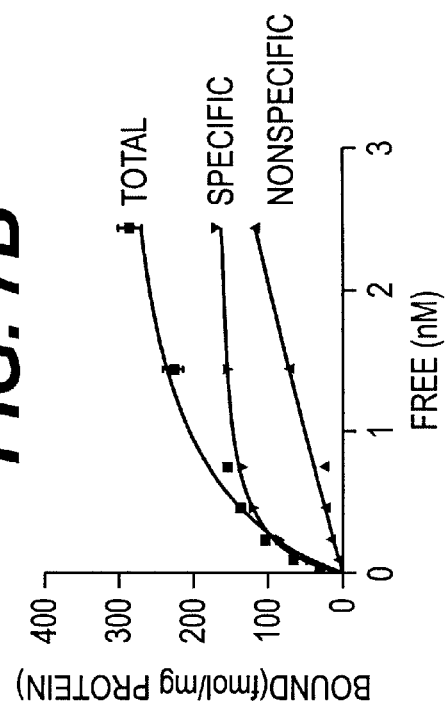
FIG. 7B
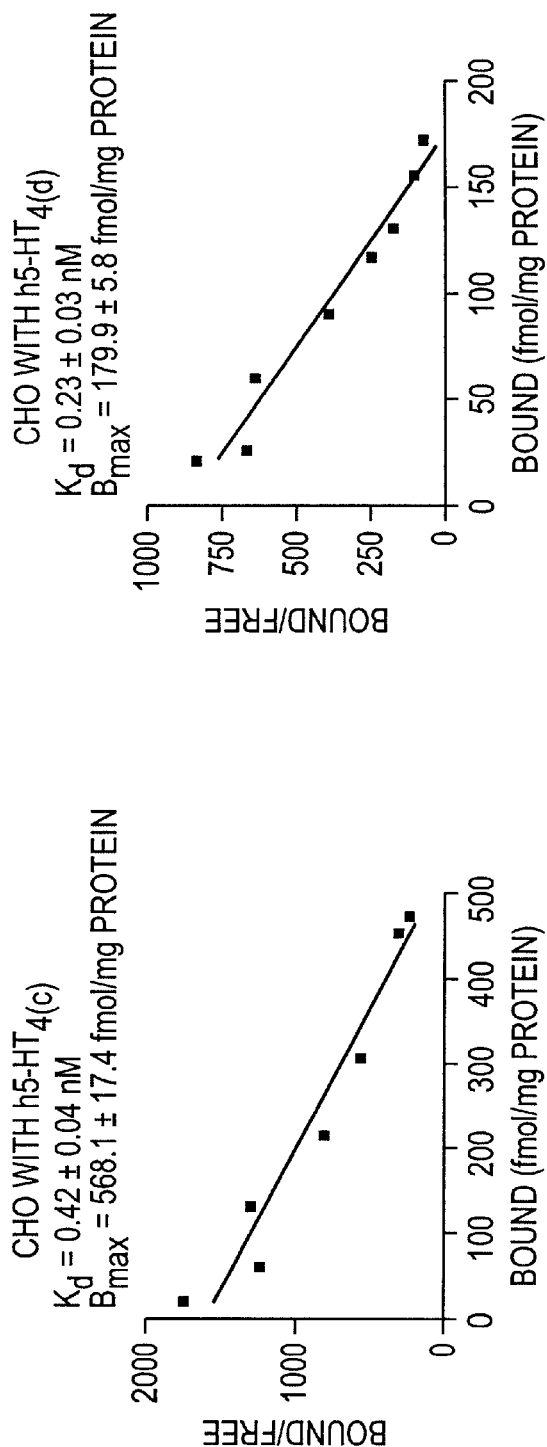
FIG. 7D
FIG. 7A
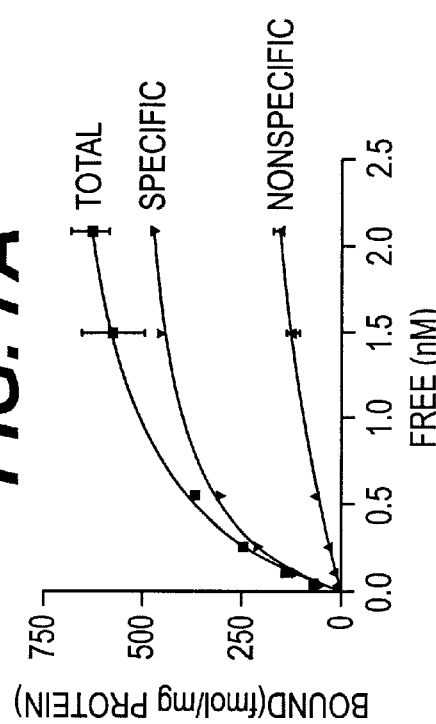
FIG. 7C

FIG. 10
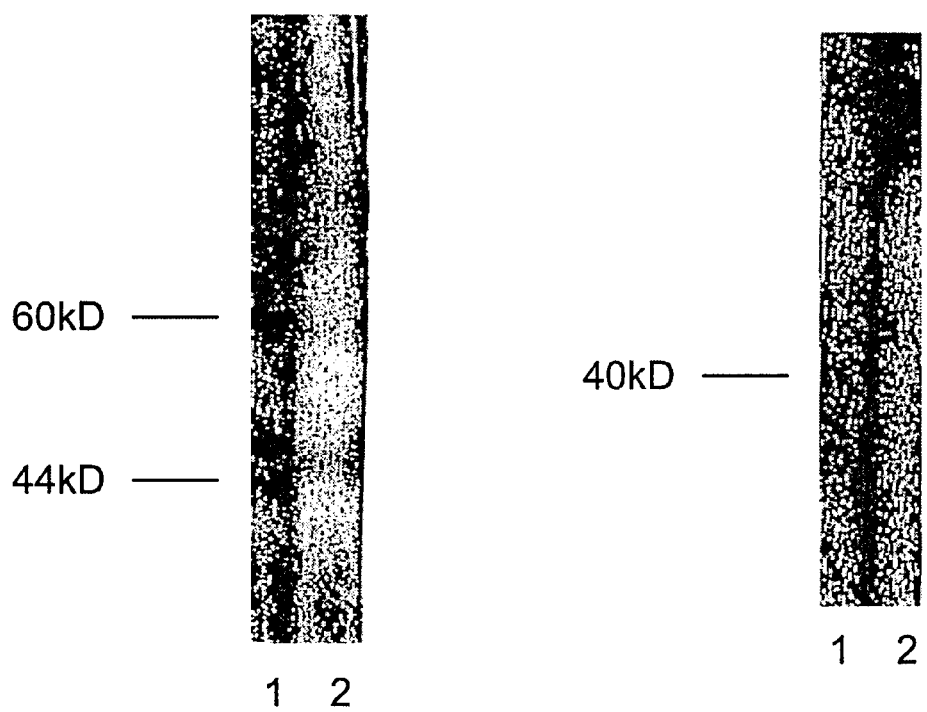
FIG. 11A  FIG. 11B

SEQUENCE LISTING

<160> NUMBER OF SEQ ID NOS: 24

<210> SEQ ID NO 1
<211> LENGTH: 1170
<212> TYPE: DNA
<213> ORGANISM: Homo sapiens

<400> SEQUENCE: 1

```
cggtgcttat ttcctgtaat ggacaaactt gatgctaatg tgagttctga ggagggtttc      60
gggtcagtgg agaaggtggt gctgctcacg tttctctcga cggttatcct gatggccatc     120
ttggggaacc tgctggtgat ggtggctgtg tgctgggaca gcagctcag gaaaataaaa      180
acaaattatt tcattgtatc tcttgctttt gcggatctgc tggtttcggt gctggtgatg     240
cctttggtg ccattgagct ggttcaagac atctggattt atggggaggt gttttgtctt      300
gttcggacat ctctggacgt cctgctcaca acggcatcga tttttcacct gtgctgcatt     360
tctctggata ggtattacgc catctgctgc cagcctttgg tctataggaa caagatgacc     420
cctctgcgca tcgcattaat gctgggaggc tgctgggtca tccccacgtt tatttctttt     480
ctccctataa tgcaaggctg gaataacatt ggcataattg atttgataga aagaggaag      540
ttcaaccaga actctaactc tacgtactgt gtcttcatgt caacaagcc ctacgccatc      600
acctgctctg tggtggcctt ctacatccca tttctcctca tggtgctggc ctattaccgc     660
atctatgtca cagctaagga gcatgccat cagatccaga tgttacaacg ggcaggagcc      720
tcctccgaga gcaggcctca gtcggcagac cagcatagca ctcatcgcat gaggacagag     780
accaaagcag ccaagaccct gtgcatcatc atgggttgct tctgcctctg ctgggcacca     840
ttctttgtca ccaatattgt ggatcctttc atagactaca ctgtccctgg gcaggtgtgg     900
actgcttttcc tctggctcgg ctatatcaat tccgggttga acccttttct ctacgccttc    960
ttgaataagt cttttagacg tgccttcctc atcatcctct gctgtgatga tgagcgctac    1020
cgaagacctt ccattctggg ccagactgtc ccttgttcaa ccacaaccat taatggatcc    1080
acacatgtac taagttctgg aactgaaacc gacagaagaa actttggaat aaggaagaga    1140
agattgacca aaccatccta atgccaaaaa                                      1170
```

<210> SEQ ID NO 2
<211> LENGTH: 760
<212> TYPE: PRT
<213> ORGANISM: Homo sapiens

<400> SEQUENCE: 2

Met Asp Lys Leu Asp Ala Asn Val Ser Ser Glu Glu Gly Phe Gly Ser
 1               5                  10                  15

Val Glu Lys Val Val Leu Leu Thr Phe Leu Ser Thr Val Ile Leu Met
            20                  25                  30

Ala Ile Leu Gly Asn Leu Leu Val Met Val Ala Val Cys Trp Asp Arg
        35                  40                  45

Gln Leu Arg Lys Ile Lys Thr Asn Tyr Phe Ile Val Ser Leu Ala Phe
    50                  55                  60

Ala Asp Leu Leu Val Ser Val Leu Val Met Pro Phe Gly Ala Ile Glu
65                  70                  75                  80

Leu Val Gln Asp Ile Trp Ile Tyr Gly Glu Val Phe Cys Leu Val Arg
                85                  90                  95

Thr Ser Leu Asp Val Leu Leu Thr Thr Ala Ser Ile Phe His Leu Cys

```
                    100                 105                 110
Cys Ile Ser Leu Asp Arg Tyr Tyr Ala Ile Cys Cys Gln Pro Leu Val
            115                 120                 125
Tyr Arg Asn Lys Met Thr Pro Leu Arg Ile Ala Leu Met Leu Gly Gly
    130                 135                 140
Cys Trp Val Ile Pro Thr Phe Ile Ser Phe Leu Pro Ile Met Gln Gly
145                 150                 155                 160
Trp Asn Asn Ile Gly Ile Ile Asp Leu Ile Glu Lys Arg Lys Phe Asn
                165                 170                 175
Gln Asn Ser Asn Ser Thr Tyr Cys Val Phe Met Val Asn Lys Pro Tyr
            180                 185                 190
Ala Ile Thr Cys Ser Val Val Ala Phe Tyr Ile Pro Phe Leu Leu Met
        195                 200                 205
Val Leu Ala Tyr Tyr Arg Ile Tyr Val Thr Ala Lys Glu His Ala His
    210                 215                 220
Gln Ile Gln Met Leu Gln Arg Ala Gly Ala Ser Ser Glu Ser Arg Pro
225                 230                 235                 240
Gln Ser Ala Asp Gln His Ser Thr His Arg Met Arg Thr Glu Thr Lys
                245                 250                 255
Ala Ala Lys Thr Leu Cys Ile Ile Met Gly Cys Phe Cys Leu Cys Trp
            260                 265                 270
Ala Pro Phe Phe Val Thr Asn Ile Val Asp Pro Phe Ile Asp Tyr Thr
        275                 280                 285
Val Pro Gly Gln Val Trp Thr Ala Phe Leu Trp Leu Gly Tyr Ile Asn
    290                 295                 300
Ser Gly Leu Asn Pro Phe Leu Tyr Ala Phe Leu Asn Lys Ser Phe Arg
305                 310                 315                 320
Arg Ala Phe Leu Ile Ile Leu Cys Cys Asp Asp Glu Arg Tyr Arg Arg
                325                 330                 335
Pro Ser Ile Leu Gly Gln Thr Val Pro Cys Ser Thr Thr Ile Asn
            340                 345                 350
Gly Ser Thr His Val Leu Ser Ser Gly Thr Glu Thr Asp Arg Arg Asn
        355                 360                 365
Phe Gly Ile Arg Lys Arg Arg Leu Thr Lys Pro Ser Met Asp Lys Leu
    370                 375                 380
Asp Ala Asn Val Ser Ser Glu Glu Gly Phe Gly Ser Val Glu Lys Val
385                 390                 395                 400
Val Leu Leu Thr Phe Leu Ser Thr Val Ile Leu Met Ala Ile Leu Gly
                405                 410                 415
Asn Leu Leu Val Met Val Ala Val Cys Trp Asp Arg Gln Leu Arg Lys
            420                 425                 430
Ile Lys Thr Asn Tyr Phe Ile Val Ser Leu Ala Phe Ala Asp Leu Leu
        435                 440                 445
Val Ser Val Leu Val Met Pro Phe Gly Ala Ile Glu Leu Val Gln Asp
    450                 455                 460
Ile Trp Ile Tyr Gly Glu Val Phe Cys Leu Val Arg Thr Ser Leu Asp
465                 470                 475                 480
Val Leu Leu Thr Thr Ala Ser Ile Phe His Leu Cys Cys Ile Ser Leu
                485                 490                 495
Asp Arg Tyr Tyr Ala Ile Cys Cys Gln Pro Leu Val Tyr Arg Asn Lys
            500                 505                 510
Met Thr Pro Leu Arg Ile Ala Leu Met Leu Gly Gly Cys Trp Val Ile
        515                 520                 525
```

| | | | | | | | | | | | |
|---|---|---|---|---|---|---|---|---|---|---|---|
|Pro|Thr|Phe|Ile|Ser|Phe|Leu|Pro|Ile|Met|Gln|Gly|Trp|Asn|Asn|Ile|
| |530| | | | |535| | | | |540| | | | |
|Gly|Ile|Ile|Asp|Leu|Ile|Glu|Lys|Arg|Lys|Phe|Asn|Gln|Asn|Ser|Asn|
|545| | | | |550| | | | |555| | | | |560|
|Ser|Thr|Tyr|Cys|Val|Phe|Met|Val|Asn|Lys|Pro|Tyr|Ala|Ile|Thr|Cys|
| | | | |565| | | | |570| | | | |575| |
|Ser|Val|Val|Ala|Phe|Tyr|Ile|Pro|Phe|Leu|Met|Val|Leu|Ala|Tyr|
| | | | |580| | | | |585| | | | |590| |
|Tyr|Arg|Ile|Tyr|Val|Thr|Ala|Lys|Glu|His|Ala|His|Gln|Ile|Gln|Met|
| | | | |595| | | | |600| | | | |605| |
|Leu|Gln|Arg|Ala|Gly|Ala|Ser|Ser|Glu|Ser|Arg|Pro|Gln|Ser|Ala|Asp|
| |610| | | | |615| | | | |620| | | | |
|Gln|His|Ser|Thr|His|Arg|Met|Arg|Thr|Glu|Thr|Lys|Ala|Ala|Lys|Thr|
|625| | | | |630| | | | |635| | | | |640|
|Leu|Cys|Ile|Ile|Met|Gly|Cys|Phe|Cys|Leu|Cys|Trp|Ala|Pro|Phe|Phe|
| | | | |645| | | | |650| | | | |655| |
|Val|Thr|Asn|Ile|Val|Asp|Pro|Phe|Ile|Asp|Tyr|Thr|Val|Pro|Gly|Gln|
| | | | |660| | | | |665| | | | |670| |
|Val|Trp|Thr|Ala|Phe|Leu|Trp|Leu|Gly|Tyr|Ile|Asn|Ser|Gly|Leu|Asn|
| | | | |675| | | | |680| | | | |685| |
|Pro|Phe|Leu|Tyr|Ala|Phe|Leu|Asn|Lys|Ser|Phe|Arg|Arg|Ala|Phe|Leu|
| |690| | | | |695| | | | |700| | | | |
|Ile|Ile|Leu|Cys|Cys|Asp|Asp|Glu|Arg|Tyr|Arg|Arg|Pro|Ser|Ile|Leu|
|705| | | | |710| | | | |715| | | | |720|
|Gly|Gln|Thr|Val|Pro|Cys|Ser|Thr|Thr|Thr|Ile|Asn|Gly|Ser|Thr|His|
| | | | |725| | | | |730| | | | |735| |
|Val|Leu|Ser|Ser|Gly|Thr|Glu|Thr|Asp|Arg|Arg|Asn|Phe|Gly|Ile|Arg|
| | | | |740| | | | |745| | | | |750| |
|Lys|Arg|Arg|Leu|Thr|Lys|Pro|Ser|
| |755| | | | |760| |

<210> SEQ ID NO 3
<211> LENGTH: 1208
<212> TYPE: DNA
<213> ORGANISM: Homo sapiens

<400> SEQUENCE: 3

| | | |
|---|---|---|
|cggtgcttat ttcctgtaat ggacaaactt gatgctaatg tgagttctga ggagggtttc|60|
|gggtcagtgg agaaggtggt gctgctcacg tttctctcga cggttatcct gatggccatc|120|
|ttggggaacc tgctggtgat ggtggctgtg tgctgggaca gcagctcag gaaaataaaa|180|
|acaaattatt tcattgtatc tcttgctttt gcggatctgc tggtttcggt gctggtgatg|240|
|ccctttggtg ccattgagct ggttcaagac atctggattt atgggaggt gttttgtctt|300|
|gttcggacat ctctggacgt cctgctcaca acggcatcga ttttcaccct gtgctgcatt|360|
|tctctggata ggtattacgc catctgctgc cagccttgg tctataggaa caagatgacc|420|
|cctctgcgca tcgcattaat gctgggaggc tgctgggtca tccccacgtt tatttctttt|480|
|ctccctataa tgcaaggctg gaataacatt ggcataattg atttgataga aagaggaag|540|
|ttcaaccaga actctaactc tacgtactgt gtcttcatgg tcaacaagcc ctacgccatc|600|
|acctgctctg tggtggcctt ctacatccca tttctcctca tggtgctggc ctattaccgc|660|
|atctatgtca cagctaagga gcatgcccat cagatccaga tgttacaacg ggcaggagcc|720|
|tcctccgaga gcaggcctca gtcggcagac cagcatagca ctcatcgcat gaggacagag|780|

```
accaaagcag ccaagaccct gtgcatcatc atgggttgct tctgcctctg ctgggcacca      840
ttctttgtca ccaatattgt ggatcctttc atagactaca ctgtccctgg gcaggtgtgg      900
actgctttcc tctggctcgg ctatatcaat tccggttga accctttct ctacgccttc       960 ttgaataagt cttttagacg tgccttcctc atcatcctct gctgtgatga tgagcgctac     1020
cgaagacctt ccattctggg ccagactgtc ccttgttcaa ccacaaccat taatggatcc     1080
acacatgtac taagattttg agctccttga ggactgtggc caattcttat tgctcatttt     1140
ttttcttagt gcccaacaca ggtttttttg cactgaagtt atcaaataaa ttcattggat     1200
gtaaaaaa                                                              1208
```

<210> SEQ ID NO 4
<211> LENGTH: 360
<212> TYPE: PRT
<213> ORGANISM: Homo sapiens

<400> SEQUENCE: 4

```
Met Asp Lys Leu Asp Ala Asn Val Ser Ser Glu Glu Gly Phe Gly Ser
 1               5                   10                  15

Val Glu Lys Val Val Leu Leu Thr Phe Leu Ser Thr Val Ile Leu Met
                20                  25                  30

Ala Ile Leu Gly Asn Leu Leu Val Met Val Ala Val Cys Trp Asp Arg
            35                  40                  45

Gln Leu Arg Lys Ile Lys Thr Asn Tyr Phe Ile Val Ser Leu Ala Phe
        50                  55                  60

Ala Asp Leu Leu Val Ser Val Leu Val Met Pro Phe Gly Ala Ile Glu
65                  70                  75                  80

Leu Val Gln Asp Ile Trp Ile Tyr Gly Glu Val Phe Cys Leu Val Arg
                85                  90                  95

Thr Ser Leu Asp Val Leu Leu Thr Thr Ala Ser Ile Phe His Leu Cys
            100                 105                 110

Cys Ile Ser Leu Asp Arg Tyr Tyr Ala Ile Cys Cys Gln Pro Leu Val
        115                 120                 125

Tyr Arg Asn Lys Met Thr Pro Leu Arg Ile Ala Leu Met Leu Gly Gly
    130                 135                 140

Cys Trp Val Ile Pro Thr Phe Ile Ser Phe Leu Pro Ile Met Gln Gly
145                 150                 155                 160

Trp Asn Asn Ile Gly Ile Ile Asp Leu Ile Glu Lys Arg Lys Phe Asn
                165                 170                 175

Gln Asn Ser Asn Ser Thr Tyr Cys Val Phe Met Val Asn Lys Pro Tyr
            180                 185                 190

Ala Ile Thr Cys Ser Val Val Ala Phe Tyr Ile Pro Phe Leu Leu Met
        195                 200                 205

Val Leu Ala Tyr Tyr Arg Ile Tyr Val Thr Ala Lys Glu His Ala His
    210                 215                 220

Gln Ile Gln Met Leu Gln Arg Ala Gly Ala Ser Ser Glu Ser Arg Pro
225                 230                 235                 240

Gln Ser Ala Asp Gln His Ser Thr His Arg Met Arg Thr Glu Thr Lys
                245                 250                 255

Ala Ala Lys Thr Leu Cys Ile Ile Met Gly Cys Phe Cys Leu Cys Trp
            260                 265                 270

Ala Pro Phe Phe Val Thr Asn Ile Val Asp Pro Phe Ile Asp Tyr Thr
        275                 280                 285
```

```
Val Pro Gly Gln Val Trp Thr Ala Phe Leu Trp Leu Gly Tyr Ile Asn
    290                 295                 300

Ser Gly Leu Asn Pro Phe Leu Tyr Ala Phe Leu Asn Lys Ser Phe Arg
305                 310                 315                 320

Arg Ala Phe Leu Ile Ile Leu Cys Cys Asp Asp Glu Arg Tyr Arg Arg
                325                 330                 335

Pro Ser Ile Leu Gly Gln Thr Val Pro Cys Ser Thr Thr Ile Asn
            340                 345                 350

Gly Ser Thr His Val Leu Arg Phe
        355                 360

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Phe Gly Ala Ile Glu Leu Val Gln Asp Ile Trp Ile Tyr Gly Glu Val
  1               5                  10                  15

Phe Cys Leu Val Arg Thr Ser Leu Asp Val
                20                  25

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Gly Ile Ile Cys Leu Ile Glu Lys Arg Lys Phe Asn Gln Asn Ser Asn
  1               5                  10                  15

Ser Thr Tyr Cys Val
                20

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Cys Gly Gln Trp Glu Ser Gln Asx His Pro Pro Ala Thr Ser Pro Leu
  1               5                  10                  15

Val Ala Ala Gln Pro Ser Asp Thr
                20

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Tyr Gly His His Gln Glu Leu Glu Lys Leu Pro Ile His Asn Asp Pro
  1               5                  10                  15
```

```
Glu Ser Leu Glu Ser Cys Phe
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Cys Gly Thr Glu Thr Asp Arg Arg Asn Phe Gly Ile Arg Lys Arg Arg
  1               5                  10                  15

Leu Thr Lys Pro Ser
            20

<210> SEQ ID NO 10
<211> LENGTH: 8
<212> TYPE: PRT
<213> ORGANISM: Artificial Sequence
<220> FEATURE:
<221> NAME/KEY: OTHER
<222> LOCATION: (2)..(2)
<223> OTHER INFORMATION: Xaa in position 2 = aminohexanoic acid

<400> SEQUENCE: 10

Cys Xaa Thr His Val Leu Arg Phe
  1               5

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 11
cggtgcttat ttcctgtaat g                                           21

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 12
atggtcaaca agccctac                                               18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 13
gcctcaggtg aagagaat                                               18

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer
```

```
<400> SEQUENCE: 14
tggcattagg atggtttggt ca                                              22

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 15
gcaataagaa ttggccac                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 16
gtcttctggg tcattgtc                                                   18

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 17
ttaggatggt ttggtca                                                    17

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 18
ctcaaggagc tcaaaatc                                                   18

<210> SEQ ID NO 19
<211> LENGTH: 30
<212> TYPE: PRT
<213> ORGANISM: Homo sapiens

<400> SEQUENCE: 19

Leu Arg Tyr Thr Val Leu His Arg Gly His His Gln Glu Leu Glu Lys
1               5                   10                  15
Leu Pro Ile His Asn Asp Pro Glu Ser Leu Glu Ser Cys Phe
            20                  25                  30

<210> SEQ ID NO 20
<211> LENGTH: 30
<212> TYPE: PRT
<213> ORGANISM: Rattus rattus

<400> SEQUENCE: 20

Leu Arg Tyr Thr Val Leu His Ser Gly Gln His Gln Glu Leu Glu Lys
1               5                   10                  15
Leu Pro Ile His Asn Asp Pro Glu Ser Leu Glu Ser Cys Phe
```

```
                         20                  25                  30

<210> SEQ ID NO 21
<211> LENGTH: 31
<212> TYPE: PRT
<213> ORGANISM: Homo sapiens

<400> SEQUENCE: 21

Leu Arg Asp Ala Val Glu Cys Gly Gly Gln Trp Glu Ser Gln Cys His
1               5                  10                  15

Pro Pro Ala Thr Ser Pro Leu Val Ala Ala Gln Pro Ser Asp Thr
                20                  25                  30

<210> SEQ ID NO 22
<211> LENGTH: 49
<212> TYPE: PRT
<213> ORGANISM: Rattus rattus

<400> SEQUENCE: 22

Leu Arg Asp Thr Val Glu Cys Gly Gly Gln Trp Glu Ser Arg Cys His
1               5                  10                  15

Leu Thr Ala Thr Ser Pro Leu Val Ala Ala Gln Pro Val Ile Arg Arg
                20                  25                  30

Pro Gln Asp Asn Asp Leu Glu Asp Ser Cys Ser Leu Lys Arg Ser Gln
            35                  40                  45

Ser

<210> SEQ ID NO 23
<211> LENGTH: 23
<212> TYPE: PRT
<213> ORGANISM: Homo sapiens

<400> SEQUENCE: 23

Leu Ser Ser Gly Thr Glu Thr Asp Arg Arg Asn Phe Gly Ile Arg Lys
1               5                  10                  15

Arg Arg Leu Thr Lys Pro Ser
                20

<210> SEQ ID NO 24
<211> LENGTH: 380
<212> TYPE: PRT
<213> ORGANISM: Homo sapiens

<400> SEQUENCE: 24

Met Asp Lys Leu Asp Ala Asn Val Ser Ser Glu Glu Gly Phe Gly Ser
1               5                  10                  15

Val Glu Lys Val Val Leu Leu Thr Phe Leu Ser Thr Val Ile Leu Met
                20                  25                  30

Ala Ile Leu Gly Asn Leu Leu Val Met Val Ala Val Cys Trp Asp Arg
            35                  40                  45

Gln Leu Arg Lys Ile Lys Thr Asn Tyr Phe Ile Val Ser Leu Ala Phe
        50                  55                  60

Ala Asp Leu Leu Val Ser Val Leu Val Met Pro Phe Gly Ala Ile Glu
65                  70                  75                  80

Leu Val Gln Asp Ile Trp Ile Tyr Gly Glu Val Phe Cys Leu Val Arg
                85                  90                  95

Thr Ser Leu Asp Val Leu Leu Thr Thr Ala Ser Ile Phe His Leu Cys
            100                 105                 110

Cys Ile Ser Leu Asp Arg Tyr Tyr Ala Ile Cys Cys Gln Pro Leu Val
```

-continued

```
                  115                 120                 125
Tyr Arg Asn Lys Met Thr Pro Leu Arg Ile Ala Leu Met Leu Gly Gly
        130                 135                 140

Cys Trp Val Ile Pro Thr Phe Ile Ser Phe Leu Pro Ile Met Gln Gly
145                 150                 155                 160

Trp Asn Asn Ile Gly Ile Ile Asp Leu Ile Glu Lys Arg Lys Phe Asn
                165                 170                 175

Gln Asn Ser Asn Ser Thr Tyr Cys Val Phe Met Val Asn Lys Pro Tyr
            180                 185                 190

Ala Ile Thr Cys Ser Val Val Ala Phe Tyr Ile Pro Phe Leu Leu Met
        195                 200                 205

Val Leu Ala Tyr Tyr Arg Ile Tyr Val Thr Ala Lys Glu His Ala His
        210                 215                 220

Gln Ile Gln Met Leu Gln Arg Ala Gly Ala Ser Ser Glu Ser Arg Pro
225                 230                 235                 240

Gln Ser Ala Asp Gln His Ser Thr His Arg Met Arg Thr Glu Thr Lys
                245                 250                 255

Ala Ala Lys Thr Leu Cys Ile Ile Met Gly Cys Phe Cys Leu Cys Trp
            260                 265                 270

Ala Pro Phe Phe Val Thr Asn Ile Val Asp Pro Phe Ile Asp Tyr Thr
        275                 280                 285

Val Pro Gly Gln Val Trp Thr Ala Phe Leu Trp Leu Gly Tyr Ile Asn
        290                 295                 300

Ser Gly Leu Asn Pro Phe Leu Tyr Ala Phe Leu Asn Lys Ser Phe Arg
305                 310                 315                 320

Arg Ala Phe Leu Ile Ile Leu Cys Cys Asp Asp Glu Arg Tyr Arg Arg
                325                 330                 335

Pro Ser Ile Leu Gly Gln Thr Val Pro Cys Ser Thr Thr Thr Ile Asn
            340                 345                 350

Gly Ser Thr His Val Leu Ser Ser Gly Thr Glu Thr Asp Arg Arg Asn
        355                 360                 365

Phe Gly Ile Arg Lys Arg Arg Leu Thr Lys Pro Ser
370                 375                 380
```

SPLICE VARIANTS FOR HUMAN 5-HT$_4$ SEROTONIN RECEPTOR AND THEIR APPLICATIONS, IN PARTICULAR FOR SCREENING

The present invention relates to novel splicing variants of the serotoninergic receptor 5-HT$_4$ in humans.

BACKGROUND OF THE INVENTION

Serotonin (5-hydroxytryptamine or 5-HT) is a neurotransmitter which is located in the central and peripheral nervous system of vertebrates, where it exerts various physiological roles mediated by different receptor subtypes (Saxena, 1995). The receptors 5-HT$_4$ represent a member of the family of receptors with seven transmembrane (7TM) domains coupled to a G protein which is positively coupled to adenylate cyclase (Hedge and Eglen, 1996). The receptors 5-HT$_4$ are expressed in a wide variety of tissues, including the human brain and the rodent brain (Eglen et al., 1995), the human, dog, pig and rodent gastro-intestinal tract, and the pig and human heart (Hedge and Eglen, 1996). In the mammalian brain, the receptors 5-HT$_4$ contribute to dopamine secretion (Bonhomme et al., 1995) and regulate learning and long-term memory via the modification of acetylcholine release (Marchetti-Gauthier et al., 1997). In the peripheral tissues, the receptors 5-HT$_4$ have proven to regulate gastro-intestinal tract motility, intestinal electrolyte secretion, adrenal secretion of corticosteroides, bladder contraction and atrium contractility (Edge and Eglen, 1996).

The receptors 5-HT$_4$ are involved in a wide variety of central and peripheral disorders, including cardiac arrhythmias (Kaumann, 1994) and neurodegenerative disorders (Reynolds et al., 1996; Wong et al., 1996). In addition, the development of receptor 5-HT$_4$ agonists and antagonists may have therapeutic applications in the central nervous system for treating neuropsychiatric disorders associated with a dysfunction of the central dopaminergic system, such as Parkinson's disease (Bonhomme et al., 1995), or for treating amnesic deficiencies as presented in patients suffering from Alzheimer's disease (Marchetti-Gauthier et al., 1997). Such medicines might also be useful for treating peripheral disorders such as irritable bowel syndrome, gastroparesia, urinary incontinence and cardiac arrhythmias (Hedge and Eglen, 1996).

The receptors 5-HT$_4$ present a unique pharmacology which is clearly different from that of the other members of the 5-HT receptor family (Ford and Clarke, 1993). Most pharmacological and transductional studies on the receptors 5-HT$_4$ have been carried out on the central nervous system and gastro-intestinal tract of rodents and in porcine and human hearts (Eglen et al., 1995; Hedge and Eglen, 1996). Although the pharmacology of the receptors 5-HT$_4$ present in these preparations is very similar, unexplained differences exist. Thus, benzamides, such as renzapride and cisapride, behave as potent and total agonists of the receptors 5-HT$_4$ in mouse colliculi neurons, but are less potent and only partial agonists in the human heart (Ford and Clarke, 1993; Hoyer et al., 1994) and the detrusor muscle isolated from human bladder (Ford and Clarke, 1993, Hoyer et al., 1994; Candura et al., 1996). 5-Methoxytryptamine (5-MeOT), which is a 5-HT$_4$ agonist, has an unusually weak agonist action on the receptors 5-HT$_4$ of the human detrusor muscle (Candura et al., 1996). ML10302, an agonist of the receptor 5-HT$_4$ which imitates the effect of 5-HT on the relaxation of rat oesophagus, and on electrically-induced contraction in guinea pig ileum (Langlois et al., 1994), has a weak agonist effect combined with a net antagonism of 5-HT-on the cAMP response generated by the human receptor 5-HT$_{4(a)}$ cloned from human atrium (Blondel et al., 1997), and an antagonist effect in colliculus neurons (Ansanay et al., 1996). In addition, the desensitization mechanisms for the receptors 5-HT$_4$ are tissue-dependent. Specifically, a homologous rapid and total desensitization (cAMP-independent) of the receptors 5-HT$_4$ is observed in mouse colliculi neurons (Ansanay et al., 1996) and rat oesophagus (Ronde et al., 1996), whereas this type of receptor is desensitized to a lesser degree in the human atrium (Kaumann et al., 1991).

The first receptor 5-HT$_4$ was cloned from rat brain (Gerald et al., 1995), and two splicing variants (r5-HT$_{4S}$ and r5-HT$_{4L}$) were identified. These variants differ in the lengths and the sequence of the carboxy-terminal end. The long form (r5-HT$_{4L}$), which has also been cloned in mouse colliculi neurons (m5-HT$_{4L}$), has transcripts in approximately each part of the brain (Claeysen et al., 1996). An interesting observation comes from the peripheral distribution of the transcripts of r5-HT$_{4L}$ and r5-HT$_{4S}$ in rats. Whereas both forms are expressed in the gastro-intestinal tract (ileum and colon), only the r5-HT$_{4S}$ transcript is found in the heart (Gerald et al., 1995). In addition, Sr-HT$_{4S}$ has been found exclusively in the atrium (Gerald et al., 1995). The human homologues of the receptors r5-HT$_{4S}$ and r5-HT$_{4L}$, herein termed h5-HT$_{4(a)}$ and h5-HT$_{4(b)}$, have recently been cloned. The receptor h5-HT$_{4(a)}$ was cloned from human heart (Blondel et al., 1997; Claeysen et al., 1997); the receptor h5-HT$_{4(b)}$ was cloned from a library (Van de Wyngaert et al., 1997). These two receptors h5-HT$_{4(a)}$ and h5-HT$_{4(b)}$, when transiently expressed in COS-7 cells, present a conventional 5-HT$_4$ pharmacological profile. However, the affinities of the cloned receptor h5-HT$_{4(a)}$ for agonists such as ML10302, BIMU1, renzapride and zacopride are lower than those found in the brain.

The inventors have now shown the existence of two novel serotonin receptor subtypes in humans, termed receptors h5-HT$_{4(c)}$ and h5-HT$_{4(d)}$.

The analysis of the sequence homologies suggests that forms h5-HT$_{4(c)}$ and h5-HT$_{4(b)}$ are respectively the human correspondents of forms r5-HT$_{4S}$ and r5-HT$_{4L}$ in rats, whereas forms h5-HT$_{4(c)}$ and h5-HT$_{4(d)}$ represent two novel isoforms of the receptor. The isoform h5-HT$_{4(c)}$ presents a high number of putative phosphorylation sites (one for protein kinase C, one for protein kinase A/protein kinase G and two for casein kinase II), all contained in the last 25 residues of the amino acid sequence.

The phosphorylation of the carboxy-terminal end of seven-transmembrane-domained receptors by protein kinase A regulates the desensitization of the receptor and the association of the receptor with G protein in response to increasing concentrations of cAMP (Dohlman et al., 1991).

In addition, in seven-transmembrane-domained receptors such as the $\beta_1$- and $\beta_2$-adrenergic receptors (Pei et al., 1994; Freedman et al., 1995) and the receptor 5-HT$_{2c}$ (Westphal et al., 1995), the phosphorylation of the receptor by non-cAMP-dependent protein kinases such as the β-adrenergic receptor kinases (βARK1 and βARK2) or rhodopsin kinase allows substrate-activated homologous desensitization. The number and nature of the phosphorylation sites present at the C-terminal end of the receptor 5-HT$_4$ splicing variants are thus capable of influencing the negative regulation of receptor function.

Tissue-dependent differences in receptor 5-HT$_4$ desensitization mechanisms have been reported (Ford and Clarke, 1993), and may be related to the restricted profiles of the expression of the receptor 5-HT$_4$ isoforms in the various tissues. Thus, the receptor 5-HT$_4$ desensitization mechanism in mouse colliculi neurons resembles that described for β-adrenergic receptors, and appears to be independent of the cAMP pathway. It has been proposed that a "βARK-like" kinase mediates the specific phosphorylation of the receptor 5-HT$_4$ in these neuronal cells (Ford and Clarke, 1993). C-terminal phosphorylation of the isoform 5-HT$_{4(c)}$ by casein kinase II or PKC might thus explain the cAMP-independent desensitization observed in these cells.

The form 5-HT$_{4(d)}$ is characterized by a very short C-terminal end, with a coding sequence which finishes two amino acids after Leu$_{358}$. Similarities in structure between the 5-HT$_4$ C-terminal ends and the 5-HT$_7$ C-terminal end (same number of variants, including a phosphorylation site-rich isoform and a truncated isoform close to the splicing site), despite the absence of a clear sequence homology, suggest similarities in the regulation of functional activity among the 5-HT receptors which are positively coupled to adenylate cyclase.

SUMMARY OF THE INVENTION

A subject of the present invention is an isolated polypeptide constituting splicing variants of the human serotoninergic receptor, the amino acid sequence of which is chosen from the sequence SEQ ID No. 2 of the variant polypeptide 5-HT$_{4(c)}$ and the sequence SEQ ID No. 4 of the variant polypeptide 5-HT$_{4(d)}$, and any biologically active polypeptide fragment or derivative of this polypeptide.

The present invention thus concerns more particularly an isolated polypeptide constituting the human serotoninergic receptor of type 5-HT$_{4(c)}$. More particularly, a subject of the invention is a polypeptide h5-HT$_{4(c)}$ having the amino acid sequence SEQ ID No. 2, or any biologically active polypeptide fragment or derivative of this polypeptide.

A subject of the present invention is also an isolated polypeptide constituting the human serotoninergic receptor of type 5-HT$_{4(d)}$. More particularly, a subject of the invention is a polypeptide h5-HT$_{4(d)}$ having the amino acid sequence SEQ ID No. 4, or any biologically active polypeptide fragment or derivative of this polypeptide.

The sequence SEQ ID No. 2 represents the amino acid sequence of the polypeptide h5-HT$_{4(c)}$ and the sequence SEQ ID No. 4 represents the amino acid sequence of the polypeptide h5-HT$_{4(d)}$.

"Derivative" is intended to mean any variant polypeptide of the polypeptide of sequence SEQ ID No. 2 or No. 4, or any molecule resulting from a modification of genetic and/or chemical nature of the sequence SEQ ID No. 2 or No. 4, i.e. obtained by mutation, deletion, addition, substitution and/or chemical modification of a single or of a limited number of amino acids, as well as any isoform sequence, i.e. a sequence which is identical to the sequence SEQ ID No. 2 or No. 4 or to one of its modified sequences or fragments, and which contains one or more amino acids in the form of a D enantiomer, said variant, modified or isoform sequences having conserved at least one of the properties which make them biologically active.

The expression "biologically active" means that the compound to which it relates is capable of binding to serotonin or to serotonin-related ligands and/or of participating in serotonin-induced signal transduction at the cell membrane, in particular in adenylate cyclase activation, and/or is capable of inducing antibodies which recognize the polypeptide h5-HT$_{4(c)}$ or h5-HT$_{4(d)}$ according to the invention. Examples of serotonin-related ligands are in particular 5-methoxytryptamine, GR113808, BIMU1, etc.

The invention thus also comprises any polypeptide having an amino acid sequence which is essentially identical to the sequence SEQ ID No. 2 or No. 4, in which one or more residues have been constitutively substituted with a similar functional residue, and which demonstrates its suitability in mimicking the receptor h5-HT$_{4(c)}$ or h5-HT$_{4(d)}$ as described in the present invention. Examples of conservative substitutions include substituting a hydrophobic residue such as isoleucine, valine, leucine or methionine with another hydrophobic residue, substituting a polar hydrophilic residue such as arginine with lysine, glutamine with asparagine, or glycine with serine, substituting a basic residue such as lysine, arginine or histidine with another basic residue or substituting an acid residue such as aspartic acid or glutamic acid with another acid residue.

Similarly, the invention comprises any polypeptide having one or more residues which are chemically derived by reaction of a functional group. The polypeptides of the present invention also include any polypeptide having one or more additions and/or deletions of residues with respect to the sequence SEQ ID No. 2 or No. 4, as long as the biological activity is maintained.

The polypeptides h5-HT$_{4(c)}$ and h5-HT$_{4(d)}$ of the present invention can be synthesized by all the methods well known to persons skilled in the art, including the recombinant DNA techniques. The polypeptides h5-HT$_{4(c)}$ or h5-HT$_{4(d)}$ can be synthesized by the techniques of synthetic chemistry, such as Merrifield-type synthesis, which is advantageous for reasons of purity, of antigenic specificity and of absence of undesired by-products, and for its ease of production.

A subject of the invention is also the isolated nucleotide sequence chosen from the sequence SEQ ID No. 1, the sequence SEQ ID No. 3, the nucleotide sequences derived from the sequence SEQ ID No. 1 or from the sequence SEQ ID No. 3 due to the degeneracy of the genetic code, to mutation, to deletion or to insertion, and the nucleotide sequences which are capable of specifically hybridizing with the sequence SEQ ID No. 1 or the sequence SEQ ID No. 3.

The sequence SEQ ID No. 1 represents the nucleotide sequence of the polypeptide h5-HT$_{4(c)}$ and the sequence SEQ ID No. 3 represents the nucleotide sequence of the polypeptide h5-HT$_{4(d)}$.

The various nucleotide sequences of the invention may or may not be of artificial origin. They can be DNA or RNA sequences which are obtained by screening sequence libraries by means of probes developed on the basis of the sequence SEQ ID No. 1 or No. 3. Such libraries can be prepared by conventional techniques of molecular biology which are known to persons skilled in the art.

The nucleotide sequences according to the invention can also be prepared by chemical synthesis or by mixed methods including the chemical or enzymatic modification of sequences obtained by screening libraries.

These nucleotide sequences allow the production of nucleotide probes which specifically hybridize with a sequence SEQ ID No. 1 or No. 3 according to the invention. The suitable hybridization conditions correspond to the conditions of temperature and of ionic strength usually used by persons skilled in the art, preferably to temperature conditions between ($T_m$ minus 5° C.) and ($T_m$ minus 30° C.), and more preferably to temperature conditions between ($T_m$ minus 5° C.) and ($T_m$ minus 10° C.) (high stringency), $T_m$ being the theoretical melting temperature, which is defined as being the temperature at which 50% of the paired strands separate. Such probes also form part of the invention. They can be used as diagnostic tools in vitro for detecting, by hybridization experiments, in particular "in situ" hybridization experiments, transcripts specific for the polypeptides of the invention in biological samples, or for detecting aberrant syntheses or genetic abnormalities resulting from a polymorphism, from mutations or from incorrect splicing.

The probes of the invention comprise a minimum of 10 nucleotides, and preferably at least 14 nucleotides, preferentially at least 20 nucleotides, more preferentially at least 50 nucleotides, and at the maximum comprise all of the nucleotide sequence SEQ ID No. 1 or SEQ ID No. 3 or of their complementary strands. In order to hybridize specifically with the sequences SEQ ID No. 1 or SEQ ID No. 3 encoding the receptors h5-$HT_{4(c)}$ or h5-$HT_{4(d)}$ respectively, and not with the nucleotide sequences encoding the receptors h5-$HT_4$ (a) or h5-$HT_{4(b)}$, the probes according to the invention should contain a sequence specific for the 3' end of the sequences SEQ ID No. 1 or No. 3 which encodes the C-terminal ends of the receptors h5-$HT_{4(c)}$ or h5-$HT_{4(d)}$.

Preferably, the probes of the invention are labelled prior to their use. For this, several techniques are easily accessible to persons skilled in the art, such as for example fluorescent, radioactive, chemiluminescent or enzymatic labelling.

The in vitro diagnostic methods in which these nucleotide probes are used for detecting aberrant syntheses or genetic abnormalities, such as loss of heterozygosis or gene rearrangement, in the nucleic acid sequences encoding a polypeptide h5-$HT_{4(c)}$ or h5-$HT_{4(d)}$ or a biologically active fragment are included in the present invention.

A subject of the invention is also a method for detecting the expression of the human receptor 5-$HT_{4(c)}$ or 5-$HT_{4(d)}$ in a cell or tissue sample, comprising the steps consisting in:
preparing the RNA of said sample;
bringing said RNA obtained into contact with a probe having a nucleotide sequence which is capable of specifically hybridizing with respectively the sequence SEQ ID No. 1 or the sequence SEQ ID No. 3 as defined above;
detecting the presence of mRNA which hybridizes with this probe, which indicates the expression of the receptor h5-$HT_{4(c)}$ or h5-$HT_{4(d)}$.

A subject of the invention is also a method for detecting the expression of the human receptor 5-$HT_{4(c)}$ or 5-$HT_{4(d)}$ in cells or a tissue by in situ hybridization, comprising the steps consisting in:
bringing said cells or said tissue into contact with a probe having a nicleotide sequence which is capable of specifically hybridizing with respectively the sequence SEQ ID No. 1 or the sequence SEQ ID No. 3 as defined above;
detecting the presence of mRNA which hybridizes with this probe, which indicates the expression of the receptor 5-$HT_{4(c)}$ or 5-$HT_{4(d)}$.

The cDNA probes of the invention can also advantageously be used for detecting chromosomal abnormalities.

The nucleotide sequences of the invention are also useful for the manufacture and the use of sense and/or antisense oligonucleotide primers for sequencing reactions or specific amplification reactions according to the so-called PCR (polymerase chain reaction) technique or any other variant of this technique.

The nucleotide sequences according to the invention have, moreover, uses in the therapeutic field, for preparing antisense sequences which are capable of specifically hybridizing with a nucleic acid sequence, including a messenger RNA, and which can be used in gene therapy. A subject of the invention is thus antisense sequences which are capable of at least partially inhibiting the production of polypeptides 5-$HT_{4(c)}$ or 5-$HT_{4(d)}$ as described above. Such sequences advantageously consist of those which constitute the reading frame encoding 5-$HT_{4(c)}$ or 5-$HT_{4(d)}$ in the transcript.

The nucleotide sequences according to the invention can, moreover, be used for producing recombinant polypeptides with a receptor 5-$HT_{4(c)}$ or 5-$HT_{4(d)}$, as defined above, activity.

These polypeptides can be produced from the nucleotide sequences defined above, according to techniques for producing recombinant products known to persons skilled in the art.

According to one embodiment of the invention, the nucleotide sequence can be inserted into an expression vector in which it is linked, in an effective manner, to elements which allow the regulation of its expression, such as in particular transcription terminators and/or promoters.

The signals which control the expression of the nucleotide sequences (promoters, activators, termination sequences, etc.) are chosen as a function of the host cell used. To this end, the nucleotide sequences according to the invention can be inserted into vectors which replicate autonomously in the chosen host or vectors which integrate into the chosen host. Such vectors will be prepared according to the methods currently used by persons skilled in the art, and the clones resulting therefrom can be introduced into a suitable host by standard methods, such as for example electroporation or calcium phosphate precipitation.

The cloning and/or expression vectors as described above, which contain one of the nucleotide sequences defined according to the invention, also form part of the present invention. Such an expression vector can be in particular a plasmid (such as pRc/CMV, which is available from Invitrogen, Carlsbad, Calif., or pUC18, which is available from Pharmacia, Piscataway, N.J.), a cosmid, a phage (such as the Lambda phage) or any type of recombinant virus.

The invention is also directed towards the host cells which are transiently or stably transfected by these expression vectors. These cells can be obtained by introducing into prokaryotic or eukaryotic host cells a nucleotide sequence which is inserted into a vector as defined above, and then culturing said cells under conditions which allow the replication and/or expression of the transfected nucleotide sequence.

Examples of host cells include, in particular, mammalian cells such as COS-7, CHO, NIH3T3, HeLa, LM(tk⁻), HEK293, etc. cells. The host cells can be in particular cell lines such as C6 glioma cells.

A subject of the invention is thus more particularly the cell lines which stably express the polypeptide 5-$HT_{4(c)}$ or 5-$HT_{4(d)}$ according to the invention.

Preferably, but not exclusively, the host cells for the expression of the functional recombinant receptor 5-$HT_{4(c)}$ or 5-$HT_{4(d)}$ express endogenous or recombinant G proteins and adenylate cyclases.

The host cells according to the invention can be used in a method for producing a polypeptide 5-$HT_{4(c)}$ or 5-$HT_{4(d)}$, this being a method in which cells transfected according to the invention are cultured under conditions which allow the expression of a polypeptide of sequence SEQ ID No. 2 of No. 4, or any biologically active fragment or derivative of this polypeptide, said biologically active polypeptide, fragment or derivative of this polypeptide is recovered, and then it is purified.

The purification methods used are known to persons skilled in the art. The recombinant polypeptide obtained can be purified from cell lysates and extracts, from the culture medium supernatant, by methods used individually or in combination, such as fractionation, the chromatography methods, the techniques of immunoaffinity using specific mono- or polyclonal antibodies, etc.

A subject of the invention is also poly- or monoclonal antibodies or fragments thereof, or chimeric or immunoconjugated antibodies. These antibodies or fragments are characterized in that they are obtained from a receptor polypeptide as defined above, derivative or polypeptide fragment of this polypeptide, which is administered to an animal, and are capable of specifically recognizing a polypeptide 5-$HT_{4(c)}$ or 5-$HT_{4(d)}$.

Polyclonal antibodies can be obtained from the serum of an animal immunized against the receptor 5-$HT_{4(c)}$ or 5-$HT_{4(d)}$ according to the usual procedures.

According to one embodiment of the invention, as an antigen, a suitable peptide fragment can be used which can be coupled, via a reactive residue, to a protein or another peptide bearing a T-dependent epitope. Rabbits are immunized with the equivalent of 1 mg of the peptide antigen according to the procedure described by Benoit et al (1982). At four-week intervals, the animals are treated with injections of 200 $\mu$g of antigen, and bled 10 to 14 days later. After the third injection, the antiserum is examined so as to determine its capacity for binding to the iodine-radiolabelled peptide antigen, which is prepared by the chloramine-T method, and is then purified by chromatography on a carboxymethylcellulose (CMC) ion exchange column. The antibody molecules are then collected from the mammals and isolated to the desired concentration by the methods which are well known to persons skilled in the art, for example using DEAE Sephadex to obtain the IgG fraction.

Another protocol for obtaining polyclonal antibodies is described in Example 8.

To increase the specificity of the polyclonal serum, the antibodies can be purified by immunoaffinity chromatography using solid phase-immunizing polypeptides. The antibody is brought into contact with the solid phase-immunizing polypeptide for a sufficient length of time, so as to immunoreact the polypeptide with the antibody molecule to form a solid phase immunological complex.

The monoclonal antibodies can be obtained according to the conventional method of hybridoma culture described by Köhler and Milstein (1975).

The antibodies or antibody fragments of the invention are for example chimeric antibodies, humanized antibodies, or Fab and F(ab')2 fragments. They can also be in the form of immunoconjugates or of labelled antibodies. For example, they can be combined with a toxin, such as the diphtheria toxin, or a radioactive product. In this case, these immunotoxins may constitute therapeutic agents which can be used for treating certain pathologies involving an overexpression of the receptor 5-$HT_{4(c)}$ or 5-$HT_{4(d)}$.

The antibodies of the invention, in particular the monoclonal antibodies, can also be used for the immunohistochemical analysis of the receptors 5-$HT_{4(c)}$ or 5-$HT_{4(d)}$ on specific-tissue sections, for example by immunofluorescence, gold labelling, immunoperoxidase, etc.

The anti-5-$HT_{4(c)}$ or anti-5-$HT_{4(d)}$ antibodies can be advantageously used in any situation where the expression of the receptor 5-$HT_{4(c)}$ or 5-$HT_{4(d)}$ must be observed (abnormal overexpression, monitoring the regulation of the membrane expression, etc.).

The invention also concerns a method for diagnosing in vitro an abnormal accumulation or expression of receptor 5-$HT_{4(c)}$ or 5-$HT_{4(d)}$ in a biological sample, and/or for measuring the expression level of this receptor in said sample, comprising bringing at least one antibody as defined above into contact with said biological sample under conditions which allow the possible formation of specific immunological complexes between a receptor 5-$HT_{4(c)}$ or 5-$HT_{4(d)}$ and said antibody(ies) and detecting the specific immunological complexes possibly formed.

A subject of the invention is also a kit for diagnosing in vitro an abnormal expression of the receptor 5-$HT_{4(c)}$ or 5-$HT_{4(d)}$ in a biological sample and/or for measuring the expression level of the receptor 5-$HT_{4(c)}$ or 5-$HT_{4(d)}$ in said sample comprising:

at least one antibody specific for the receptor 5-$HT_{4(c)}$ or 5-$HT_{4(d)}$, optionally bound to a support;

means for revealing the formation of specific antigen/antibody complexes between the receptor 5-$HT_{4(c)}$ or 5-$HT_{4(d)}$ and said antibody, and/or means for quantifying these complexes.

A subject of the invention is also the use of the polypeptide 5-$HT_{4(c)}$ or 5-$HT_{4(d)}$ according to the invention for detecting the presence of anti-receptor autoantibodies in pathologies associated with the dysfunction of the receptors.

A subject of the invention is also a pharmaceutical composition comprising a receptor 5-$HT_{4(c)}$ or 5-$HT_{4(d)}$ polypeptide, derivative or polypeptide fragment as defined above, a nucleotide sequence as defined above, or an antibody as defined above, combined with a pharmaceutically acceptable vehicle.

A subject of the invention is in particular a pharmaceutical composition which contains an antibody directed against the receptor 5-$HT_{4(c)}$ or 5-$HT_{4(d)}$, in sufficient amount to block the binding of the natural substrates to the receptor 5-$HT_{4(c)}$ or 5-$HT_{4(d)}$, and a pharmaceutically acceptable vehicle.

A pharmaceutical composition according to the invention in particular can be administered orally, parenterally, intravenously, intramuscularly, subcutaneously, percutaneously, or by intranasal administration.

The preparation of pharmaceutical compositions which contain active principles dissolved or dispersed in these latter is well known to persons skilled in the art. Generally, these compositions are prepared in the form of injectable solutions or suspensions. However, they can also be in solid forms which are suitable for extemporaneously preparing solutions or suspensions. The preparations can also be emulsified.

The methods of administration, the doses and the galenic forms of the pharmaceutical compositions according to the invention can be determined according to the criteria which are generally taken into account for establishing a therapeutic treatment suited to a patient, such as for example the age or the bodyweight of the patient, the seriousness of his/her general state, the tolerance to the treatment and the observed side effects, etc.

A subject of the invention is also a therapeutic treatment method for an individual suffering from complaints or disorders which are lessened, or even eliminated, by reducing the expression of the receptors 5-$HT_{4(c)}$ or 5-$HT_{4(d)}$, said method comprising administering to said individual an effective amount of the pharmaceutical composition as described above. The binding of the antibody to the receptor 5-$HT_{4(c)}$ or 5-$HT_{4(d)}$ in fact prevents the activation of the receptor and thus neutralizes the effects of an abnormal overexpression of these receptors.

A subject of the invention is also a method for screening compounds which are capable of binding to the polypeptide 5-HT$_{4(c)}$ or 5-HT$_{4(d)}$ according to the invention, in which said compounds are brought into contact with said polypeptide 5-HT$_{4(c)}$ or 5-HT$_{4(d)}$, and the degree of binding between said compounds and said polypeptide 5-HT$_{4(c)}$ or 5-HT$_{4(d)}$ is evaluated.

A large number of compounds can thus be rapidly screened to test the capacity of these compounds for binding to the receptor 5-HT$_{4(c)}$ or 5-HT$_{4(d)}$ according to the invention.

These binding assays can also be used for determining the presence or absence of serotonin in a biological sample, as well as for isolating novel endogenous ligands.

A subject of the invention is thus also a method for identifying ligands of the receptor 5-HT$_{4(c)}$ or 5-HT$_{4(d)}$ comprising the steps consisting in:

a) bringing a biological sample which is likely to contain ligands of the receptor into contact with a polypeptide 5-HT$_{4(c)}$ or 5-HT$_{4(d)}$ or a host cell expressing said polypeptide, b) isolating the ligand-receptor complexes formed, c) identifying the ligands of the receptor 5-HT$_{4(c)}$ or 5-HT$_{4(d)}$.

A subject of the invention is also a method for diagnosing in vitro an abnormal accumulation or expression of serotonin or analogues thereof in a biological sample, and/or for measuring its (their) expression level in said sample, comprising bringing a polypeptide according to the invention into contact with said biological sample under conditions which allow the formation of specific immunological complexes between said polypeptide and serotonin or analogues thereof, and detecting the specific immunological complexes formed.

The binding assays used in the context of the present invention can be carried out according to methods well known to persons skilled in the art. In particular, the compounds which are capable of binding to the receptor polypeptide can be prelabelled, and can be used alone or in competition with other unlabelled compounds.

More particularly, competitive binding assays can for example be carried out, i.e. assays of ELISA or IRMA type.

In the context of the invention, labelling means can be used for detecting the receptor 5-HT$_{4(c)}$ or 5-HT$_{4(d)}$ polypeptide according to the invention, the anti-5-HT$_{4(c)}$ or anti-5-HT$_{4(d)}$ antibodies and/or the ligands of the receptor 5-HT$_{4(c)}$ or 5-HT$_{4(d)}$.

The labelling means used can be in particular a fluorescent labelling agent which binds chemically to antibodies or to antigens without denaturation, so as to form a colorant fluorochrome which is a useful immunofluorescent indicator. The labelling agent can also be an enzyme, such as peroxidase (HRP) or glucose oxidase. Radioactive elements can also be used as labelling agents.

The inventors have moreover studied the tissue distribution of the four various splicing variants of the receptor 5-HT$_4$, i.e. 5-HT$_{4(a)}$, 5-HT$_{4(b)}$, 5-HT$_{4(c)}$ and 5-HT$_{4(d)}$.

The expression profile of each splice variant of 5-HT$_4$ is not restricted to a given tissue, with the exception of 5-HT$_{4(d)}$, which is only in the intestines. Some tissues (human atrium, brain, intestine) express three or four 5-HT$_4$ isoforms, whereas others (bladder, kidney) express only one isoform. Thus, the bladder specifically expresses only the 5-HT$_{4(a)}$ form. In two tissues (ventricles of the heart and liver) no transcript encoding any 5-HT$_4$ splicing variant could be amplified. The presence of the receptor 5-HT$_{4(d)}$ exclusively in the intestines makes a potential therapeutic target thereof for treating digestive disorders associated with this receptor, without side effects on the organs expressing the other isoforms. The cerebral location of the 5-HT$_{4(c)}$ isoform, although not exclusive, makes it possible to envisage that this isoform participates in the neuronal effects of serotonin. Specifically, it has been shown that the receptors 5-HT$_4$ of mouse colliculi neurons, unlike the receptors 5-HT$_4$ of the human atrium (Kaumann et al., 1991), are rapidly desensitized in the presence of serotonin (Ansanay et al., 1996). Now, the h5-HT$_{4(c)}$ isoform is the only one to possess phosphorylation sites on its C-terminal end, making it more sensitive to homologous desensitization.

A subject of the invention is thus more particularly the use of a receptor 5-HT$_{4(c)}$ polypeptide according to the invention for screening molecules which are useful for manufacturing medicines intended for treating the disorders of the central nervous system associated with the abnormal expression of the receptor 5-HT$_{4(c)}$.

A subject of the invention is also the use of a receptor 5-HT$_{4(d)}$ polypeptide according to the invention for screening molecules which are useful for manufacturing medicines intended for treating the disorders of the gastro-intestinal tract associated with the abnormal expression of the receptor 5-HT$_{4(d)}$.

The inventors have also studied the pharmacological profile of the receptors 5-HT$_{4(c)}$ or 5-HT$_{4(d)}$ according to the invention. Whereas the 5-HT$_{4(a)}$, 5-HT$_{4(b)}$ and 5-HT$_{4(d)}$ subtypes expressed in COS-7 cells present a similar capacity for adenylate cyclase coupling when they are exposed to 5-HT, the expression of the 5-HT$_{4(c)}$ isoform gives a constitutive activation of the adenylate cyclase, which results in an increase in the basal level of cAMP. The degree of constitutive coupling is also increased by overexpressing the 5-HT$_{4(c)}$ isoform, by using more plasmid DNA for the transcription. Such a constitutive coupling has been described in several other situations, for example 1) in the metabotropic glutamate receptor family, some splicing variants being spontaneously coupled to G proteins (Prezeau et al., 1996); 2) in specific experimental or pathological mutations which lead to a constitutive activity in certain receptors (Coughlin, 1994); 3) in the overexpress on of 7-transmembrane-domained receptors (Kenakin, 1996) such as the receptor m5-HT$_{4L}$ (Claeysen et al., 1996), which leads to a constitutive activation of G$_s$.

All the receptor h5-HT$_4$ subtypes expressed in the COS-7 cells present a conventional receptor 5-HT$_4$ profile in terms of order of potency of diverse serotoninergic ligands tested (Hoyer et al., 1994). No major difference could be found between the isoforms (a), (b) and (c) as regards the affinity constants of the 5-HT$_4$ agonists and antagonists. However, the isoform (d) always presents a higher. affinity for any 5-HT$_4$ ligand tested, in comparison with the other isoforms (Table 1). Since the receptor 5-HT$_{4(d)}$ is the shortest of the four isoforms of the receptor, this result suggests that the modifications of the C-terminal protein sequence of the 5-HT$_4$ receptors can induce changes in the binding properties. The question is to know whether these modifications participate in the variability of the affinity constants for the various 5-HT$_4$ ligands observed in the various tissues of animal species (Blondel et al., 1997). Alternative mechanisms for these variabilities may include species differences for the isoforms of the receptor 5-HT$_4$ or the existence of internal splicing variants (Ullmer et al., 1995) which might more directly affect the ligand binding site.

A subject of the invention is also a method for evaluating the pharmacological properties of the compounds which are capable of binding to the receptor 5-HT$_{4(c)}$ or 5-HT$_{4(d)}$ polypeptide, termed receptor 5-HT$_{4(c)}$ or 5-HT$_{4(d)}$ ligands, comprising the steps consisting in:

a) culturing cells which express the polypeptide 5-$HT_{4(c)}$ and/or 5-$HT_{4(d)}$ in the presence of at least one receptor 5-$HT_{4(c)}$ and/or 5-$HT_{4(d)}$ ligand; and b) evaluating the capacity of the ligand for modifying signal transduction.

More particularly, the capacity of a ligand for modifying signal transduction can be evaluated by determining the concentration of intracellular cyclic AMP (cAMP) formed by the activation of adenylate cyclase, or the adenylate cyclase activity.

According to one variant of this embodiment, said cells can be advantageously cultured in the presence:

either of increasing concentrations of at least one receptor 5-$HT_{4(c)}$ or 5-$HT_{4(d)}$ ligand, the capacity for modulating signal transduction of which is desired and of a given concentration of at least one known agonist of 5-$HT_{4(c)}$ or 5-$HT_{4(d)}$;

or of increasing concentrations of at least one known agonist of 5-$HT_{4(c)}$ or 5-$HT_{4(d)}$ and of a given concentration of at least one receptor 5-$HT_{4(c)}$ or 5-$HT_{4(d)}$ ligand, the capacity for modulating signal transduction of which is desired.

The capacity of said ligand for modulating signal transduction is then evaluated by quantitatively determining the expression of said reporter gene, as a function of the concentration of said ligand.

The biological assays according to the invention as described above thus make it possible to evaluate the pharmacological profile of the tested compounds, in particular to determine whether the tested compounds are capable of acting as agonists or antagonists of the receptor 5-$HT_{4(c)}$ or 5-$HT_{4(d)}$ according to the invention.

The present inventors have thus shown that, surprisingly, ML10375, while antagonizing the 5-HT-induced cAMP response mediated by all the 5-$HT_4$ isoforms, reduces basal adenylate cyclase activity only in the cells transfected with the receptors 5-$HT_{4(c)}$ and 5-$HT_{4(d)}$. This phenomenon is mediated by a reverse agonist effect of ML10375. This phenomenon represents the first of its kind in the family of receptors 5-$HT_4$, and it suggests that the C-terminal end structure of the 7TM receptor may participate in the development of a reverse agonist effect of a given antagonist. The compound ML10375 of formula 2-(cis-3,5-dimethyl-piperidino)ethyl 4-amino-5-chloro-2-methoxybenzoate is particularly useful for preparing medicines with reverse agonist action towards the receptor 5-$HT_{4(c)}$ or 5-$HT_{4(d)}$. This reverse agonist property is different from the receptor 5-$HT_4$ selective antagonist property already known for the compound ML10375 (patent application EP 683 161). Specifically, a simple antagonist acts only by competition with the natural ligand (serotonin), by preventing the action of the latter. As for the reverse agonist, it can lower a receptor activity which is too high in the absence of natural ligand. Thus, in the case of a pathological overexpression of receptors 5-$HT_{4(c)}$ or 5-$HT_{4(d)}$ in the brain (for 5-$HT_{4(c)}$), the heart (for 5-$HT_{4(c)}$) or the digestive system (for 5-$HT_{4(c)}$ and 5-$HT_{4(d)}$), ML10375 can normalize the response by reducing the intrinsic activity of the receptors. Such an effect cannot be obtained with another molecule which would act as a simple selective antagonist of these receptors.

The examples and figures, the legends of which are below, illustrate the invention without limiting it:

LEGEND TO THE FIGURES

FIG. 1A represents the deduced amino acid sequences of the C-terminal end of the splicing variants of receptor 5-$HT_4$ in rats and humans. In both species, the sequence diverges after $Leu_{358}$. The amino acid differences between rats and humans are high-lighted. The white circles correspond to the protein kinase consensus site, the black circles to the casein kinase II consensus site and the black triangle to a protein kinase A/protein kinase G consensus site. The asterisk corresponds to the terminal stop codon.

FIG. 1B represents the compared amino acid sequences of the variants 5-$HT_{4(c)}$ and 5-$HT_{4(d)}$.

The seven potential transmembrane domains (TM1 to TM7) of the proteins are underlined, and the putative phosphorylation sites are indicated with suitable symbols.

Figure 2:
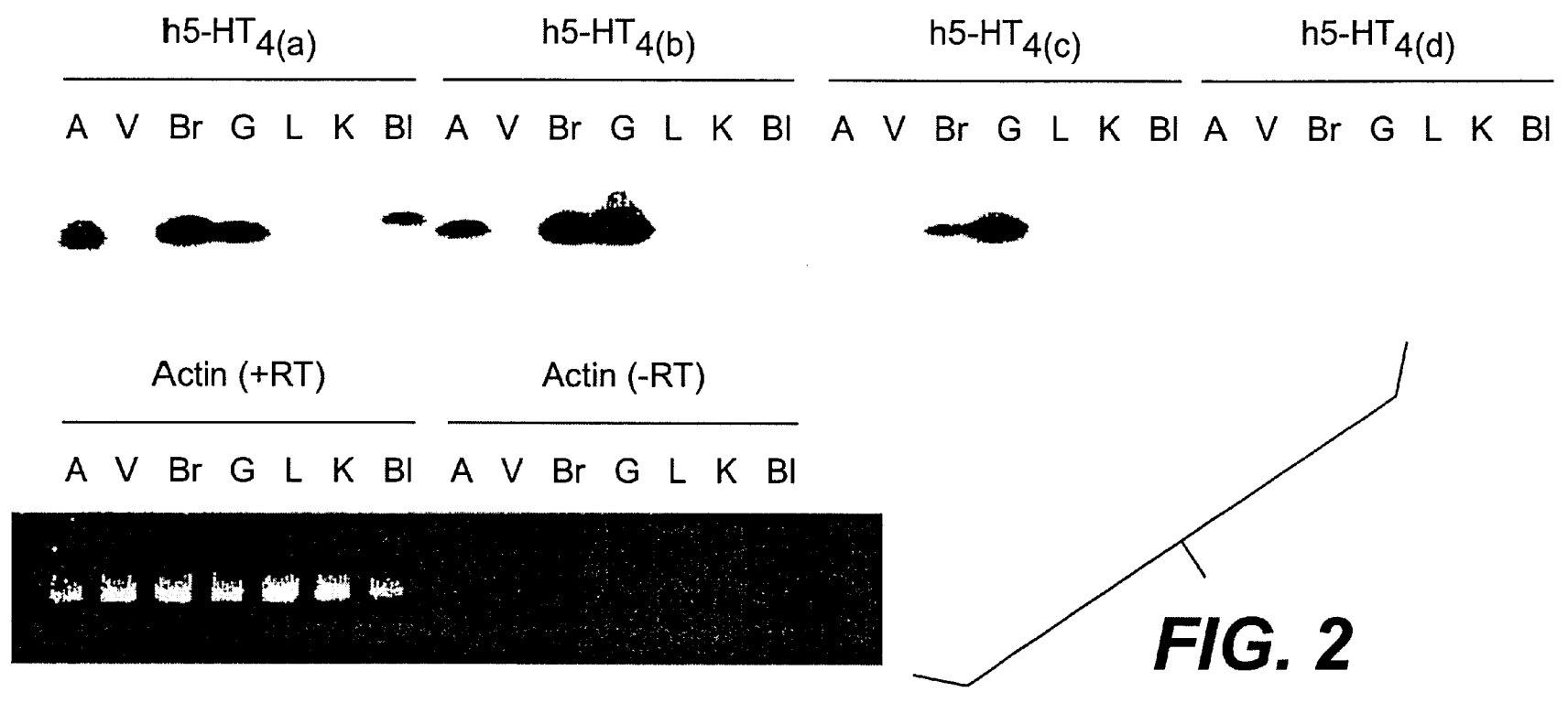

FIG. 2 represents the RT-PCR analysis carried out with 50 ng of mRNA from diverse human tissues. The PCR products were separated on a 1.5% agarose gel and analysed by Southern Blot using a specific internal oligonucleotide probe labelled with $^{32}P$, this being a primer common to 5-$HT_{4(a)}$, 5-$HT_{4(b)}$, 5-$HT_{4(c)}$ and 5-$HT_{4(d)}$. An 8-hour exposure of the autoradiograph is presented. A positive control was carried out using rat actin primers on mRNA samples treated with (+RT) or without (−RT) reverse transcriptase. The PCR products of the control experiment were analysed on a 1.5% agarose gel, and a photograph of the ethidium bromide-stained gel is presented. The PCR primers used for this analysis are described in Examples 1 and 2. (A: atrium, V: ventricle, Br: brain, G: gastro-intestinal tract, L: lung, K: kidney, Bl: bladder).

FIG. 3 represents the [$^3$H]GR113808 saturation binding analysis on membrane preparations of COS-7 cells expressing isoforms 5-$HT_{4(a)}$ (A), 5-$HT_{4(b)}$ (B), 5-$HT_{4(c)}$ (C) and 5-$HT_{4(d)}$ (D). The membranes collected from the transiently transfected COS-7 cells were incubated with 8 concentrations of [$^3$H]GR113808 (0.02–3.5 nM) for 30 minutes at. 25° C. The nonspecific binding was defined with 10 $\mu$M of ML10375. The results are from a single experiment, but are representative of three identical experiments. The $K_d$ and $B_{max}$ values are determined by computer-assisted nonlinear regression analysis (GraphPad, Prism software).

Figure 4A:
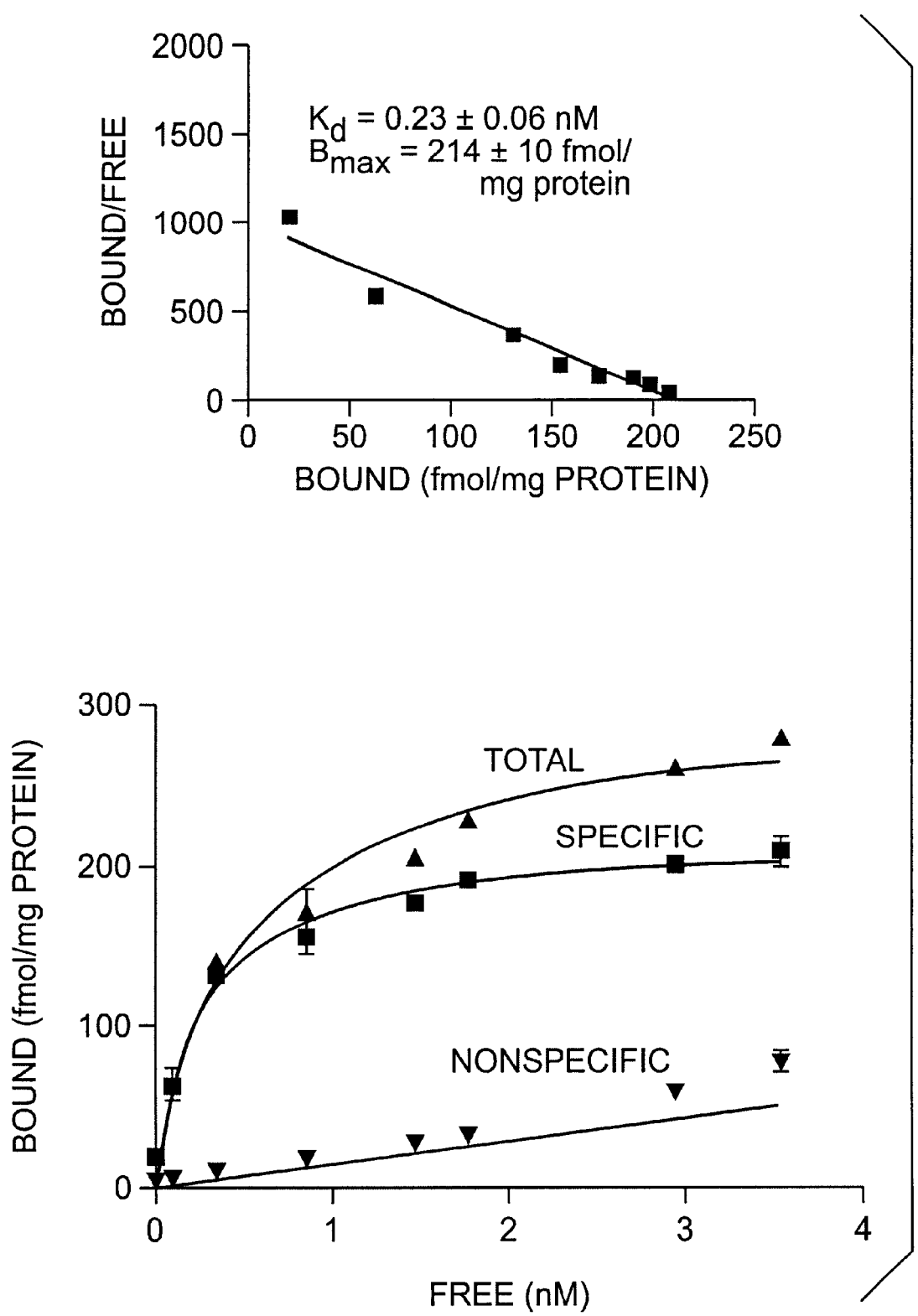
Figure 4B:
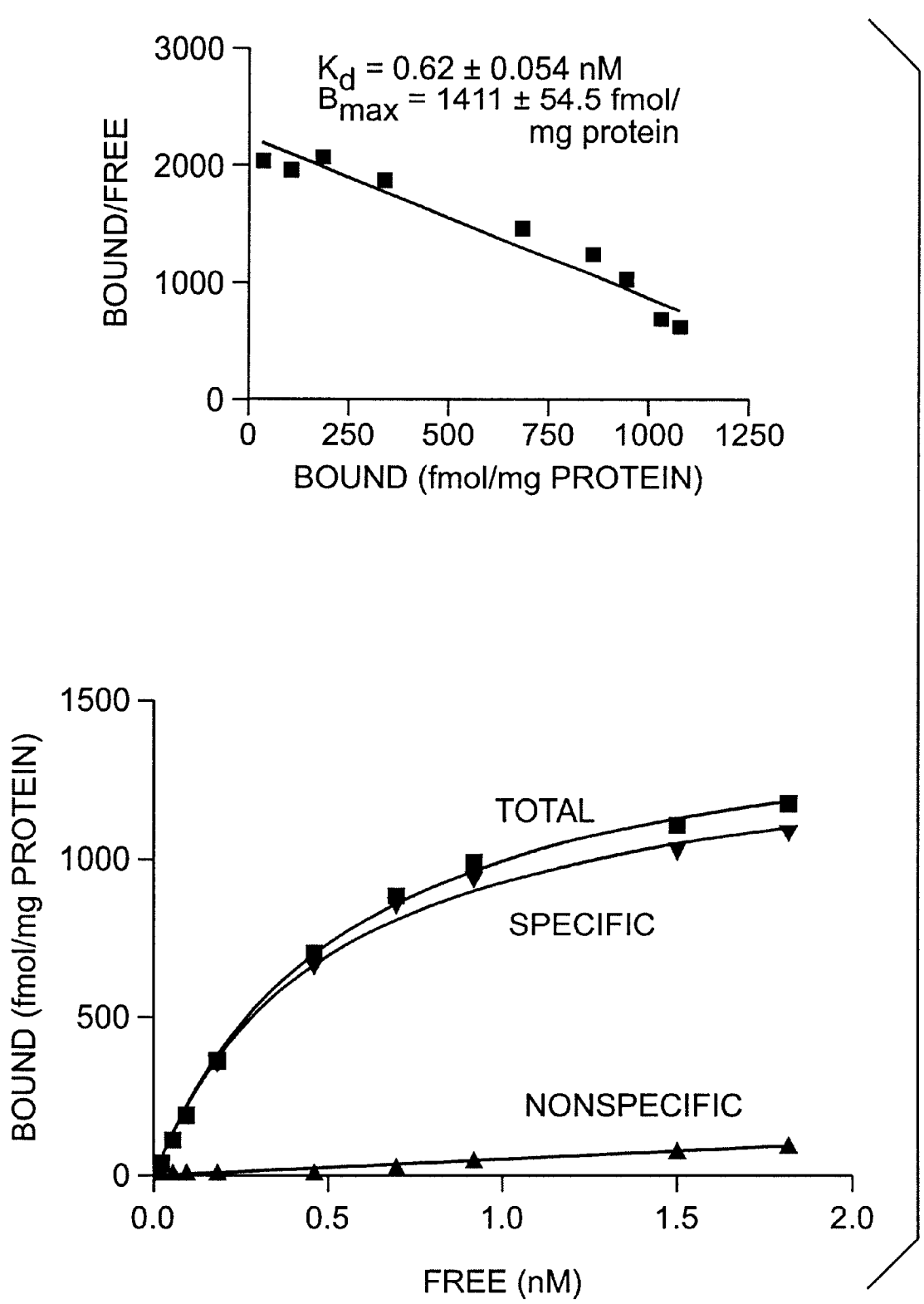
Figure 4C:
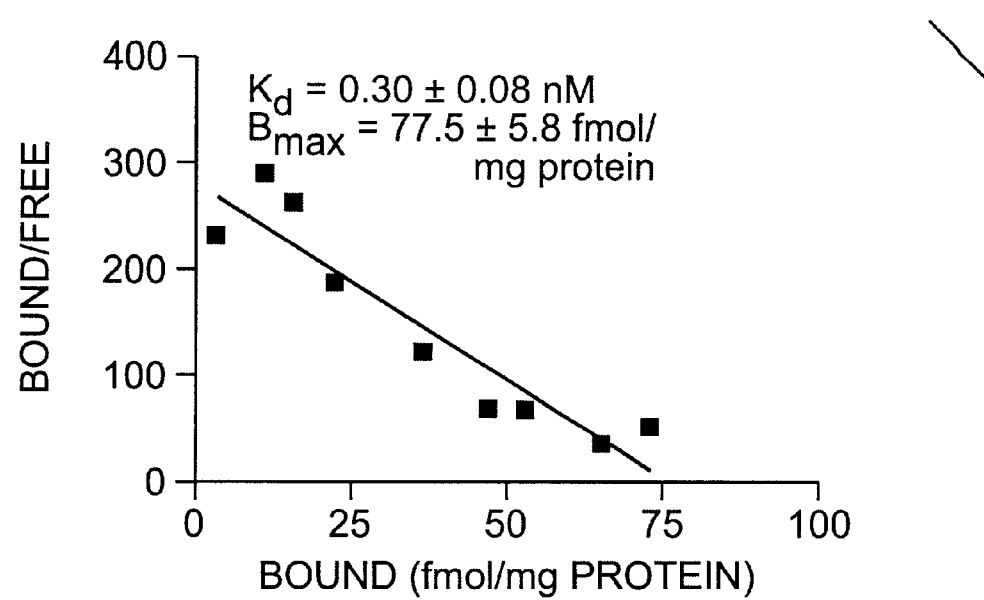
Figure 4C:
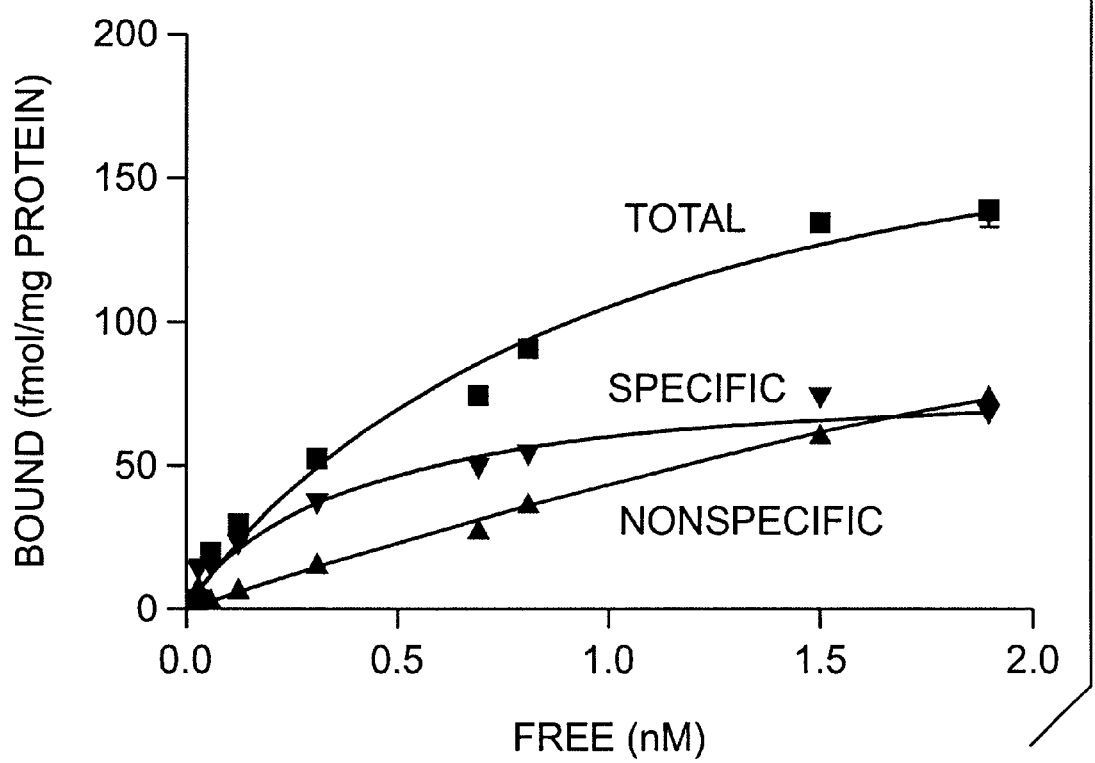
Figure 4D:
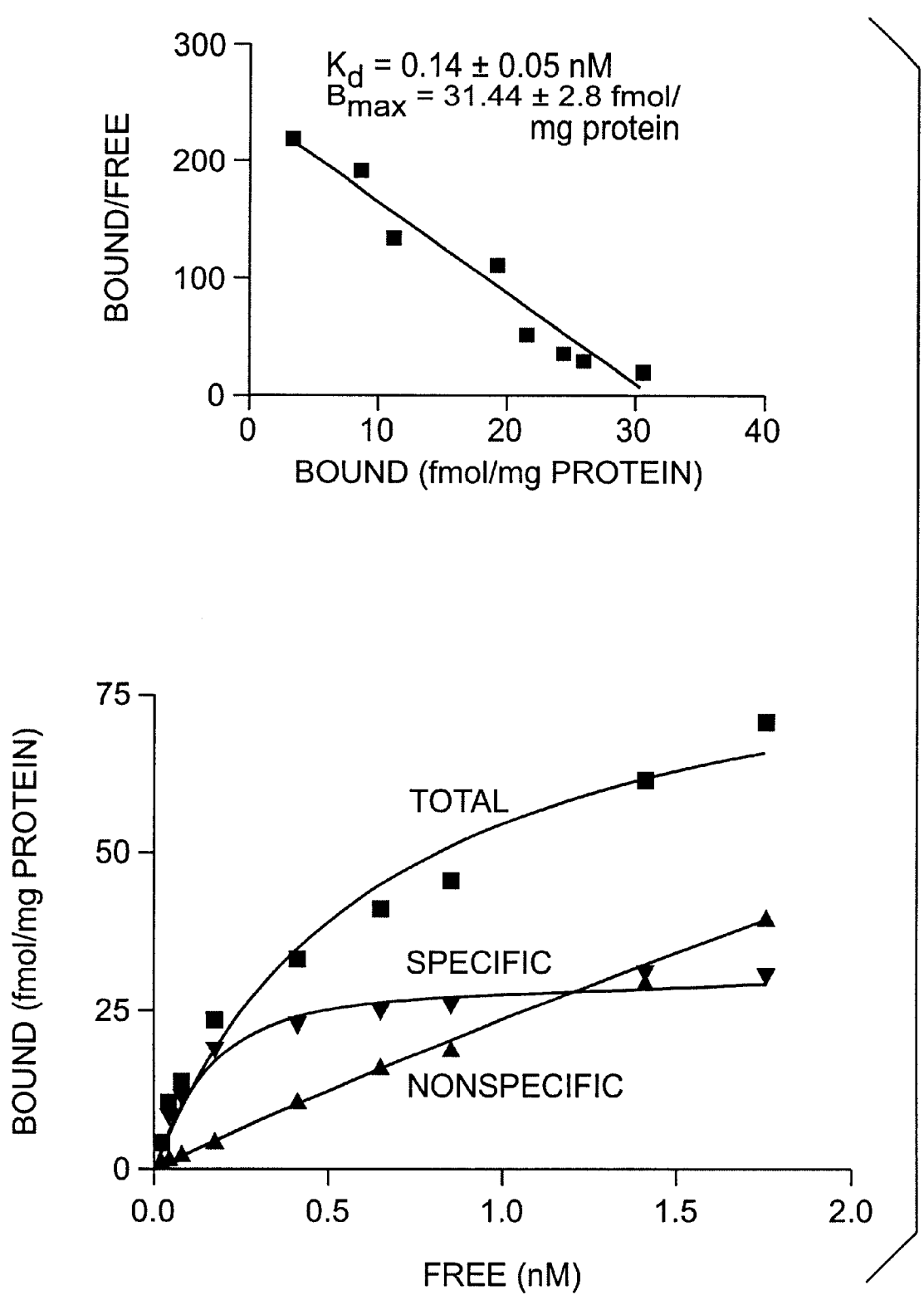

FIG. 4 represents the inhibition, by 5-HT of the specific binding of [$^3$H]GR113808 to the cloned receptors 5-$HT_{4(a)}$ (FIG. 4A), 5-$HT_{4(b)}$ (FIG. 4B), 5-$HT_{4(c)}$ (FIG. 4C) and 5-$HT_{4(d)}$ (FIG. 4D). The membranes of the transiently transfected COS-7 cells were incubated with a concentration of [$^3$H]GR113808 which was equal to 50% of the $K_d$ value of each isoform of the receptor. The nonspecific binding was defined with 10 $\mu$M ML10375. The results are presented as a percentage of specific binding in the absence of 5-HT; the data were analysed by computer-assisted nonlinear regression analysis (GraphPad, Prism software).

FIG. 5 represents the cAMP responses to diverse agonists and antagonists of the receptor 5-$HT_4$ using the receptors 5-$HT_{4(a)}$, 5-$HT_{4(b)}$, 5-$HT_{4(c)}$ and 5-$HT_{4(d)}$ transiently expressed in the COS-7 cells, or in the "blank"-transfected cells. The cells were preincubated with 5 mM theophylline and 10 $\mu$M pargyline for 15 minutes, and then incubated with 1 $\mu$M agonists (5-HT: A, C, D and E; ML10302: B and C; renzapride: B and D) and/or antagonists (ML10375: B and E), or 10 $\mu$M forskolin (A), for 15 minutes. The effect of the agonist or of the antagonist of 5-HT-induced cAMP accumulation was tested by adding the agonist or the antagonist for the 15-minute preincubation period, followed by adding 5-HT for 15 minutes. The values are mean values±SEM of 7 to 12 experiments. NS: not significant: *, $p<0.05$ and **, $p<0.01$.

FIG. 6 represents the cAMP responses of 5-HT (1 $\mu$M), of forskolin (10 $\mu$M) and of 5-$HT_4$ antagonist ML10375 (1

μM), using the receptor 5-HT$_{4(c)}$ transiently expressed in the COS-7 cells, or in the "blank"-transfected cells as control. The cells are transfected using 4 to 8 μg per well (A and B) or 6 μg per well (C and D) of plasmid DNA. The incubation conditions are identical to those described in FIGS. 5C and D: the responses are studied in the presence or absence of a 16-hour preincubation with PTX (100 ng/ml). The values are mean values±SEM of 6 to 11 experiments. NS: not significant; *, $p<0.05$ and **, $p<0.01$.

FIG. 7 represents the saturation analysis of the [$^3$H] GR113808 binding on membrane preparations of CHO cells expressing isoforms 5-HT$_{4(c)}$ (A) and 5-HT$_{4(d)}$ (B). The membranes collected from the stably transfected CHO cells were incubated with 8 concentrations of [$^3$H]GR113808 (0.01–2.5 μM) for 30 minutes at 25° C. The nonspecific binding was defined with 10 μM of ML10375. The results are from a single experiment, but are representative of three identical experiments. The $K_d$ and $B_{max}$ values (FIG. 7C and 7D) are determined by computer-assisted nonlinear regression analysis (GraphPad, Prism software).

Figure 8:
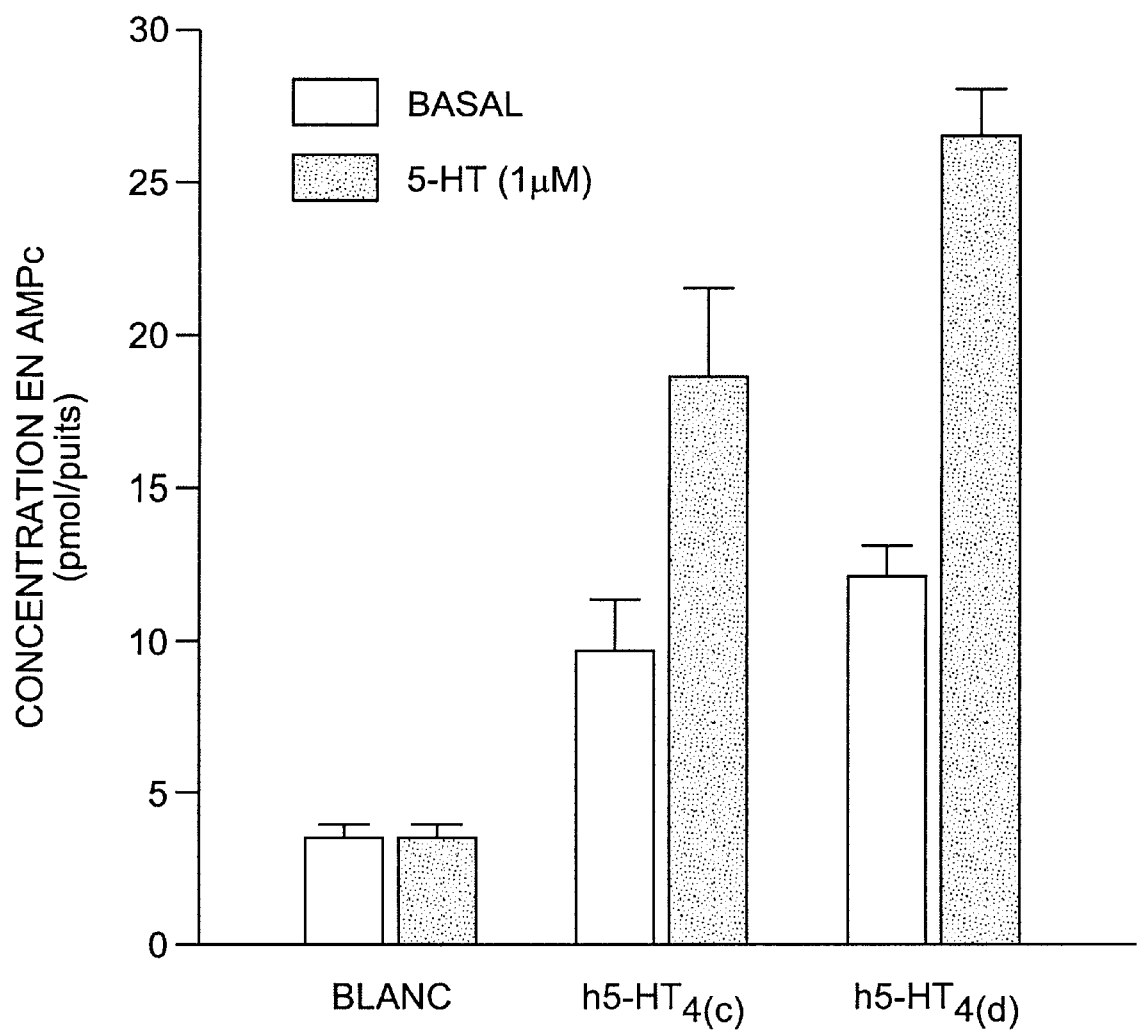

FIG. 8 represents the cAMP responses to serotonin using the receptors 5-HT$_{4(c)}$ and 5-HT$_{4(d)}$ stably expressed in the CHO cells, or in the "blank"-transfected cells. The cells were preincubated with 5 mM theophylline and 10 μM pargyline for 15 minutes, and then incubated with 1 μM 5-HT. The results are from a single experiment, but are representative of three identical experiments.

Figure 9:
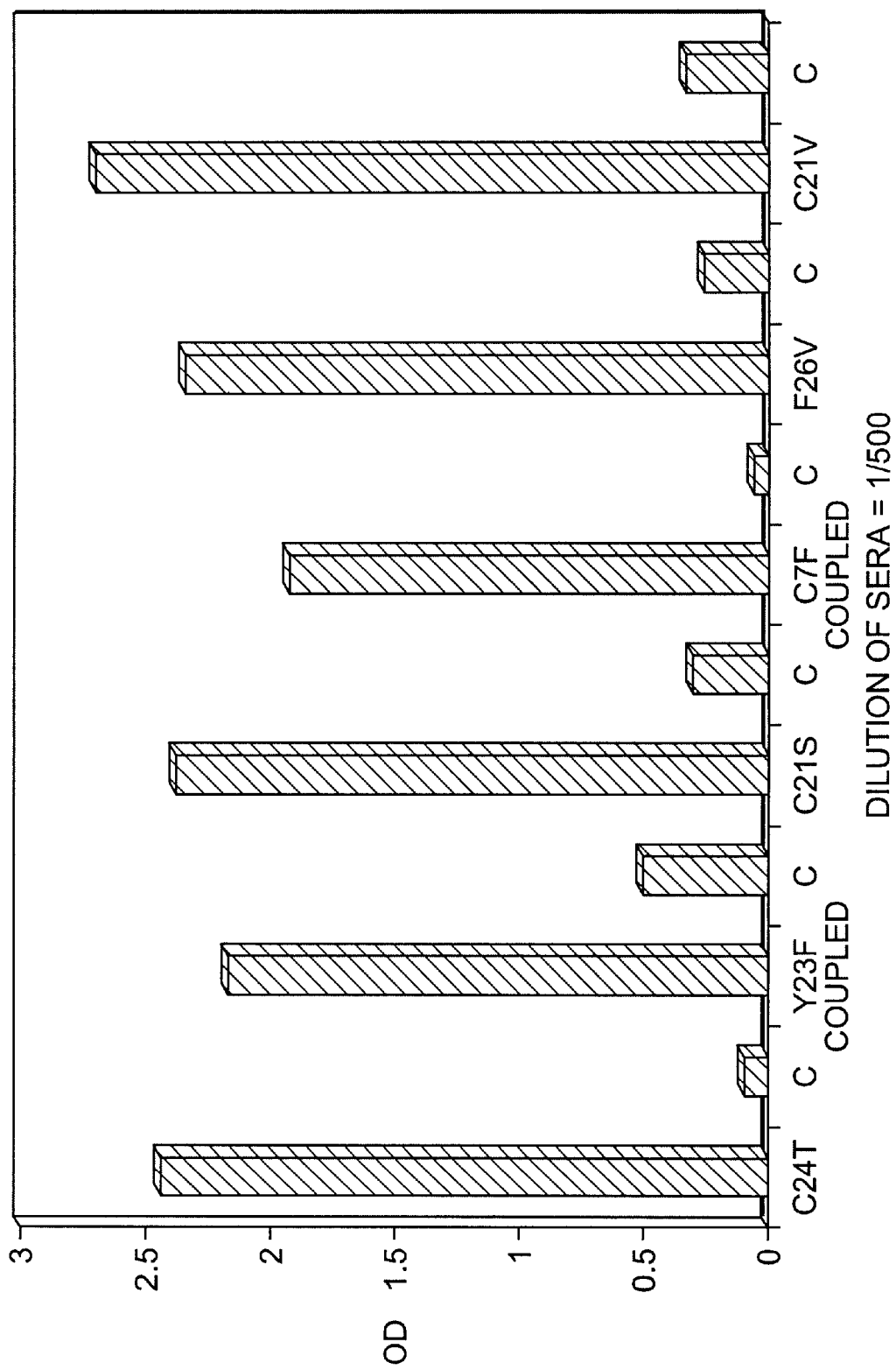

FIG. 9 represents an ELISA assay on sera from rabbits immunized with the peptides corresponding to various sequences derived from the isoforms of the receptor 5-HT$_4$. The sequences of these peptides are given in Example 8.

FIG. 9 gives the optical density values of an immunoenzymatic assay on the respective peptides adsorbed (5 μg/ml in a carbonate buffer at pH=9.5) onto MAXIsorb plates (Nunc, Denmark). The antisera were incubated for one hour at 37° C., and revealed with a peroxidase-coupled goat anti-rabbit IgG antibody conjugate (dilution ¹⁄₁₀,₀₀₀) and the substrate $H_2O_2$-ABTS (calorimetric indicator of oxidoreduction for peroxidase).

FIG. 10 demonstrates, by Western Blot, the presence of the receptor 5-HT$_4$ in the CHO cells stably expressing the 5-HT$_{4(a)}$ (line 2) and 5-HT$_{4(c)}$ (line 3) isoforms. The CHO cells were transfected with the expression vectors encoding the forms (a) and (c) of the receptor 5-HT$_4$ and selected for their neomycin resistance. Fifty μg of proteins originating from membrane extracts are separated on a 10% polyacrylamide gel, and then transferred onto nitrocellulose membrane. After incubation for 16 h in the presence of 60 μg of anti-5-HT$_4$ antibody (G21V), the blot is revealed by chemiluminescence (ECL, Amersham) and scanned. Line 1 indicates the result obtained on the control CHO cells, in which no labelling is detected; lines 2 and 3 originate from clones of CHO cells overexpressing respectively the receptor 5-HT$_{4(a)}$ and 5-HT$_{4(c)}$. A band migrating approximately with the size of 60 kDa is visualized.

FIG. 11 demonstrates, by Western Blot, the presence of the receptors h5-HT$_4$ in the CHO cells stably expressing the h5-HT$_{4(c)}$ (FIG. 11a) and 5-HT$_{4(d)}$ (FIG. 11b) isoforms. The CHO cells were transfected with the expression vectors encoding the forms (c) and (d) of the receptor h5-HT$_4$ and selected for their neomycin resistance. Sixteen μg of protein coming from CHO cells are separated on a 10% polyacrylamide gel, and then transferred onto cellulose membrane. After 16 h of incubation in the presence of 16 μg of anti-h5-HT$_{4(c)}$ (anti-C21S, FIG. 11a) or anti-5-HT$_{4(d)}$ (anti-C7F, FIG. 11b) antibodies, and in the presence (2nd line) or absence (1st line) of 50 μg of the corresponding peptides, the blots are revealed by chemiluminescence (ECL, Amersham) and scanned. The second line indicates the bands of the receptor which are nonspecific, since they are not inhibited by the corresponding peptides. The anti-C21S antibody recognizes two specific bands at 44 and 60 kDa. The anti-C7F antibody recognizes a specific band at 40 kDa. The band at 60 kDa corresponds to the glycosylated receptor and the bands at 44 and 40 kDa to the nonglycosylated receptor.

DETAILED DESCRIPTION OF THE PREFERRED EMBODIMENTS

EXAMPLE 1

Primary Structure of the Splicing Variants of the Human Receptor 5-HT$_4$

Materials:

The PCRs were carried out using a GeneAmp 2400 machine (Perkin Elmer). The Hiraq DNA polymerase and the associated buffer were obtained from Bioprobe Systems. In all the PCR reactions, the dNTps and the specific primers were at a final concentration of 200 μM and 1 μM, respectively. The double-stranded DNA was sequenced using a T7 polymerase DNA sequencing kit (Pharmacia) according to the manufacturer's instructions.

1. Rapid Amplification and Cloning of cDNA Ends

The sequence of the human receptor 5-HT$_{4(a)}$ characterized by Blondel et al., 1997 was used to synthesize the two primers HHT$_4$5[5'-CGGTGCTTATTTCCTGTMTG-3'] (SEQ ID NO. 11) and HTS3[5'-ATGGTCMCAAGCCCTAC-3'] (SEQ ID NO. 12), which correspond to the start of the sequence of the receptor and to the fifth transmembrane domain respectively. To obtain the cDNAs from the 5' ends generated by the 5-HT$_4$ gene, the anchored-RACE extension technique was used as described in Newton and Graham, 1994. 50 ng of total RNA from human brain and ileum were subjected to a reverse transcription using an oligo (dt) primer containing two anchorage sequences, and the Superscript reverse transcriptase (GIBCO/BRL). The reaction products from these two tissues were then collected and used as a matrix for a RACE reaction using the HHT$_4$5 primer with the first anchor. The product from the first PCR reaction was used as a matrix for the nested-RACE reaction using the HTS3 primer (modified to include a HindIII restriction sequence) with the second "anchor" (containing an EcoRI restriction sequence). These two PCR reactions were carried out at an average of 25 amplification cycles under the following conditions: denaturation for 1 minute at 94° C., hybridization for 1 minute at 54° C. and extension for 2 minutes at 72° C., with a final extension for 8 minutes. The hybridization temperatures were 52° C. for the RACE reaction and 54° C. for the nested-RACE reaction. The DNA fragments were separated on a 1.5% agarose gel, cloned into pGEM-7Z (cleaved with HindIII/EcoRI) and sequenced.

2. Cloning of Full Length cDNAs

The total cDNA corresponding to the splicing variants $^5$-HT$_{4(b)}$, 5-HT$_{4(c)}$ and 5-HT$_{4(d)}$ was amplified using the original reverse transcription pool from human brain and ileum and a nested-PCR strategy. The HHT$_4$5 primer (modified to include a HindIII restriction site) was used as sense primer in all the PCR reactions. The reverse primers for the first amplification cycle were F81 [5'-GCCTCAGGTGAAGAGAAT-3'] (SEQ ID NO. 13), F61 [5'-TGGCATTAGGATGGTTTGGTCA-3'] (SEQ ID NO. 14) and F71 [5'-GCAATAAGMTTGGCCAC-3'] (SEQ ID NO. 15) for 5-HT$_{4(b)}$, 5-HT$_{4(c)}$ and 5-HT$_{4(d)}$ respectively.

The reverse primers for the second amplification cycle, which all contain an EcoRI restriction site at their 5' end, were F82 [5'-GTCTTCTGGGTCATTGTC-3'] (SEQ ID NO. 16), F62 [5'-TTAGGATGGTTTGGTCA-3'] (SEQ ID NO. 17) and F72 [5'-CTCAAGGAGCTCAAAATC-3'] (SEQ ID NO. 18) for $5\text{-HT}_{4(b)}$, $5\text{-HT}_{4(c)}$ and $5\text{-HT}_{4(d)}$ respectively. The PCR conditions were the same as those used for both of the amplification cycles of RACE-PCR. The fragments corresponding to the full length cDNAs were purified on a 1.5% agarose gel, subcloned in pGEM-7Z (cleaved with HindIII/EcoRI) and sequenced to confirm the integrity of the coding sequence.

3. Primary Structure of the Splicing Variants of the Human Receptor $5\text{-HT}_4$.

The deduced amino acid sequence of the various splicing variants is illustrated in FIG. 1 starting from the splicing site $\text{Leu}_{358}$. Within this region of the receptor, $5\text{-HT}_{4(a)}$ shares 93% protein identity with the short form of the rat receptor $5\text{-HT}_{4S}$ (Blondel et al., 1997). The region between $\text{Leu}_{358}$ and the last amino acid of $5\text{-HT}_{4(b)}$ presents 74% protein identity with the corresponding region of the long form of the rat receptor $5\text{-HT}_{4L}$. However, the carboxy end of $5\text{-HT}_{4(b)}$ proved to have 18 amino acids less than its correspondent in rats, and the PKC phosphorylation consensus site described on the C-terminal side in the rat receptor $5\text{-HT}_{4L}$ is missing (Gerald et al., 1995).

The splicing variants $5\text{-HT}_{4(c)}$ and $5\text{-HT}_{4(d)}$ have never been described in any species. It is interesting to note that the carboxy end of the receptor $5\text{-HT}_{4(c)}$ presents an unusually high number of putative phosphorylation sites: two casein kinase II sites and one kinase C protein site, and a protein kinase A/protein kinase G phosphorylation consensus sequence. The $5\text{-HT}_{4(d)}$ isoform corresponds to an ultra-short form of the receptor, with a carboxy end truncation only two amino acids after the splicing site on the $\text{Leu}_{358}$.

EXAMPLE 2

Tissue Specific Expression of the Receptor $5\text{-HT}_4$ Splicing Variants

The expressions of the various $5\text{-HT}_4$ transcripts were analysed by amplification of cDNA derived from RNA isolated from diverse human tissues using a nested-RT-PCR technique. The tissue distribution was examined using two pairs of specific primers from each type of variant and two successive cycles of PCR amplification, in accordance with the conditions described in Example 1. The amplified products were identified using a specific internal oligonucleotide probe (FIG. 2). The $5\text{-HT}_{4(a)}$, $5\text{-HT}_{4(b)}$ and $5\text{-HT}_{4(c)}$ isoforms are all expressed in the atrium, the brain and the intestines. The bladder and the liver each express detectable levels of only one receptor subtype ($5\text{-HT}_{4(a)}$ and $5\text{-HT}_{4(b)}$, respectively). $5\text{-HT}_{4(d)}$ expression was detected only in the intestines. Finally, the ventricles and the lungs do not express detectable amounts of any $5\text{-HT}_4$ isoform. The presence, in all the tissues, of cDNA corresponding to the constitutively expressed β-actin gene and the absence of β-actin PCR products in control experiments without reverse transcriptase were also demonstrated (FIG. 2).

EXAMPLE 3

Pharmacological Characterization of the Receptor $5\text{-HT}_4$ Splicing Variants Transiently Expressed in COS-7 Cells Materials:

PEI (polyethyleneimine MW 800 $K_D$) was obtained from Fluka (L'Isle d'Abeau Chesnes, France). ML 10302 (2-(1-piperidyl)ethyl 4-amino-5-chloro-2-methoxy-benzoate) and ML 10375 (2-(cis-3,5-dimethyl-piperidino)ethyl 4-amino-5-chloro-2-methoxybenzoate) were synthesized according to Langlois et al., 1994; Yang et al., 1997. GR113808 (([1-[2-(methylsulphonyl)amino]ethyl]-4-piperidyl)methyl 1-methyl-1H-indole-3-carboxylate) was obtained from the Glaxo Research Group (Ware, Hertfordshire, U.K.) and [$^3$H]GR113808 was obtained from Amersham (Arlington Heights, Ill.).

1. DNA Transfection

The entire coding region of the cDNAs of $5\text{-HT}_{4(a)}$, $5\text{-HT}_{4(b)}$, $5\text{-HT}_{4(c)}$ and $5\text{-T}_{4(d)}$ was subcloned into a mammalian expression vector pRC/CMV (Invitrogen, Carlsbad, Calif.). The transfections were carried out using polyethyleneimine (PEI) as described in Boussif et al. (1995). The cells were transfected using a mixture of DNA and of PEI in a ratio of 20 μmol of PEI/mg of DNA in 0.9% NaCl. For the radioligand binding assays, the COS-7 cells were seeded into culture flasks of $1.5 \times 10^4$ mm$^2$ one day before the transfection, at a density of $1 \times 10^7$ cells/flask, incubated for six hours with plasmid DNA (150 μg/flask) and collected 48 hours after transfection. For the measurement of cAMP formation, the COS-7 cells were seeded onto twelve-well plates one day before transfection, at a density of $5 \times 10^5$ cells/well, incubated for six hours with plasmid DNA (4 to 8 μg/well according to the experiments) and assayed 24 hours after the transfection. The cells transfected with the receptor $5\text{-HT}_4$ cDNA constructs were compared with the "blank"-transfected cells, which were exposed to the unmodified pRC/CMV plasmid.

2. Membrane Preparation

Each flask of cells intended for the radioligand binding assays was washed twice with a phosphate buffer (PBS). The cells were then scraped, collected and centrifuged at 300 g for five minutes. The pellet was resuspended in 2.5 ml of ice-cold HEPES buffer (50 mM, pH 7.4) and homogenized with an Ultraturax tissue grinder. The lysate was then centrifuged at 40,000 g for 20 minutes at 4° C. The resulting pellet was resuspended in 15 volumes of HEPES buffer (50 mM, pH 7.4). The membrane preparations were maintained in ice and used within two hours for radioligand binding assays. The protein concentrations were determined by the method of Lowry et al., 1951, using bovine serum albumin as standard.

3. Radioligand Binding Assays

The radioligand binding studies were carried out in 500 μl of buffer (50 mM HEPES, pH 7.4) containing 20 μl of competitor agent (for the drug competition studies), or of ML 10375 to give a final concentration of 10 μM (for determining the nonspecific binding), or of a buffer (for determining total binding), and 20 μl of [$^3$H]GR113808 to give a final concentration of 50% of $K_d$ and 50 μl (100 to 200 μg) of membrane preparation. The saturation studies were performed using [$^3$H] GR113808 at 9 different concentrations ranging from 0.01 to 3.5 nM. The tubes were incubated at 25° C. for 30 minutes. The reaction was stopped by rapid filtration, under vacuum, through Whatman GF/B filter paper using the Brandel 48R cell harvester. The filters were presoaked in a solution of PEI (0.1%) to reduce the binding to the filters. The filters were then washed with an ice-cold buffer (50 mM Tris-HCl, pH 7.4) and placed in 4 ml of "ready safe" scintillation cocktail (Beckman, Fullerton, Calif.) overnight. The radioactivity was measured using a Beckman LS 6500 C liquid scintillation counter. The binding data were analysed by computer-assisted nonlinear regression analysis (Graph Pad Prism Program, Graph Pad Software, Inc., San Diego, Calif.).

4. Results of the Binding Assays

The saturation analysis using [$^3$H]GR113808 revealed unique high affinity sites which can be saturated for the four splicing variants of the receptor (FIG. 3). Similar $K_d$ values for [$^3$H]GR113808 were found between the four isoforms (5-HT$_{4(a)}$, 0.23±0.06; 5-HT$_{4(b)}$ 0.62±0.05; 5-HT$_{4(c)}$ 0.30±0.08; 5-HT$_{4(d)}$ 0.14±0.05 nM). However, the density of the transiently expressed receptors in the COS-7 cells ($B_{max}$) varies considerably between the transfection assays (5-HT$_{4(a)}$, 214±10; 5-HT$_{4(b)}$ 1411±55; 5-HT$_{4(c)}$ 77.5±5.8; 5-HT$_{4(d)}$ 31.4±2.8 fmol/mg of protein). The nonspecific binding increases in nonlinear fashion with the increase in ligand concentration (FIG. 3). A series of 5-HT$_4$ agonists and antagonists completely inhibits the specific binding of [$^3$H]GR113808 to all the cloned isoforms of the receptor 5-HT$_4$. All the displacement curves are monophasic, giving a Hill coefficient of 0.6 to 1.1. The data summarized in Table 1 demonstrate that the pharmacological profiles of all the cloned isoforms of the receptors 5-HT$_4$, in terms of order of potencies of the ligands tested, are very similar to those found for the receptors 5-HT$_4$ studied in situ in the human atrium (Kaumann et al., 1996) and the piglet atrium (Kaumann et al., 1995); the human striatum (Reynolds et al., 1995) and the human caudate nucleus (Waeber et al., 1993), the rat striatum (Langois et al., 1994; Yang et al., 1997) and the guinea-pig striatum (Ansanay et al., 1996), and mouse colliculi (Ansanay et al., 1996), or after expression of the cloned isoforms in cultured fibroblasts (r5-HT$_{4L}$ (Gérald et al., 1995; Adham et al., 1996); m5-HT$_{4L}$ (Claeysen et al., 1996)). It may also be noted that while each of the compounds tested bound to the isoforms a, b and c of the receptor 5-HT$_4$ with similar affinity, the affinity for the 5-HT$_{4(d)}$ isoform was usually higher by a factor of 2 to 4 (Table I).

EXAMPLE 4

Stimulation of cAMP Production by the 5-HT$_4$ Splicing Variants Transiently Expressed in COS-7 Cells Materials:

DMEM was obtained from GIBCO-BRL. Pertussis toxin (PTX) was obtained from Calbiochem. BIMUL (endo-N-8-methyl-8-azabicyclo[3.2.1]oct-3-yl)-2,3-dihydro-3-ethyl-2-oxo-1H-benzimidazole-1-carboxamide) and zacopride (4-amino-5-chloro-2-methoxy-N-(1-azabicyclo-[2,2,2]octo-3-yl)benzamide, hydrochloride) were synthesized in the laboratory by the authors of the present invention. Renzapride (BRL 24924) ((+)endo-4-amino-5-chloro-2-methoxy-N-(1-azabicyclo[3.3.1]non-4-yl)benzamide, hydrochloride) was obtained from SmithKline Beecham. 5-Hydroxylryptamine (5-HT) and 5-methoxytryptamine (5-MeOT) were obtained from Aldrich (L'Isle d'Abeau Chesnes, France) and all the other drugs were obtained from Sigma (L'Isle d'Abeau Chesnes, France).

1. Measurement of cAMP Formation

To measure intracellular cAMP accumulation, the transiently transfected COS-7 cells were incubated, 24 hours after transfection, in Dulbecco's modified Eagle medium (DMEM) containing 5 mM theophylline, 10 mM HEPES and 10 $\mu$M pargyline for 15 minutes at 37° C., in the presence of 5% $CO_2$. 5-HT (1 $\mu$M) or other serotoninergic agents (1 $\mu$M) or forskolin (10 $\mu$M) were added, and incubated for a further 15 minutes at 37° C. in the presence of 5% $CO_2$. The reaction was stopped by aspiration of the medium and addition of 500 $\mu$l of ice-cold ethanol. After one hour at room temperature, the cells were scraped, and everything was collected and freeze-dried. The pellet was resuspended in 350 $\mu$l of PBS and centrifuged for 5 min at 300 g. The cAMP was quantified in the supernatant using a radioimmunological assay (E.R.I.A. assay kit from Pasteur Diagnostics 79830). Student's t tests were carried out using the program Quick TEst.

2. Stimulation of cAMP Production

Figures 5A, 5B:
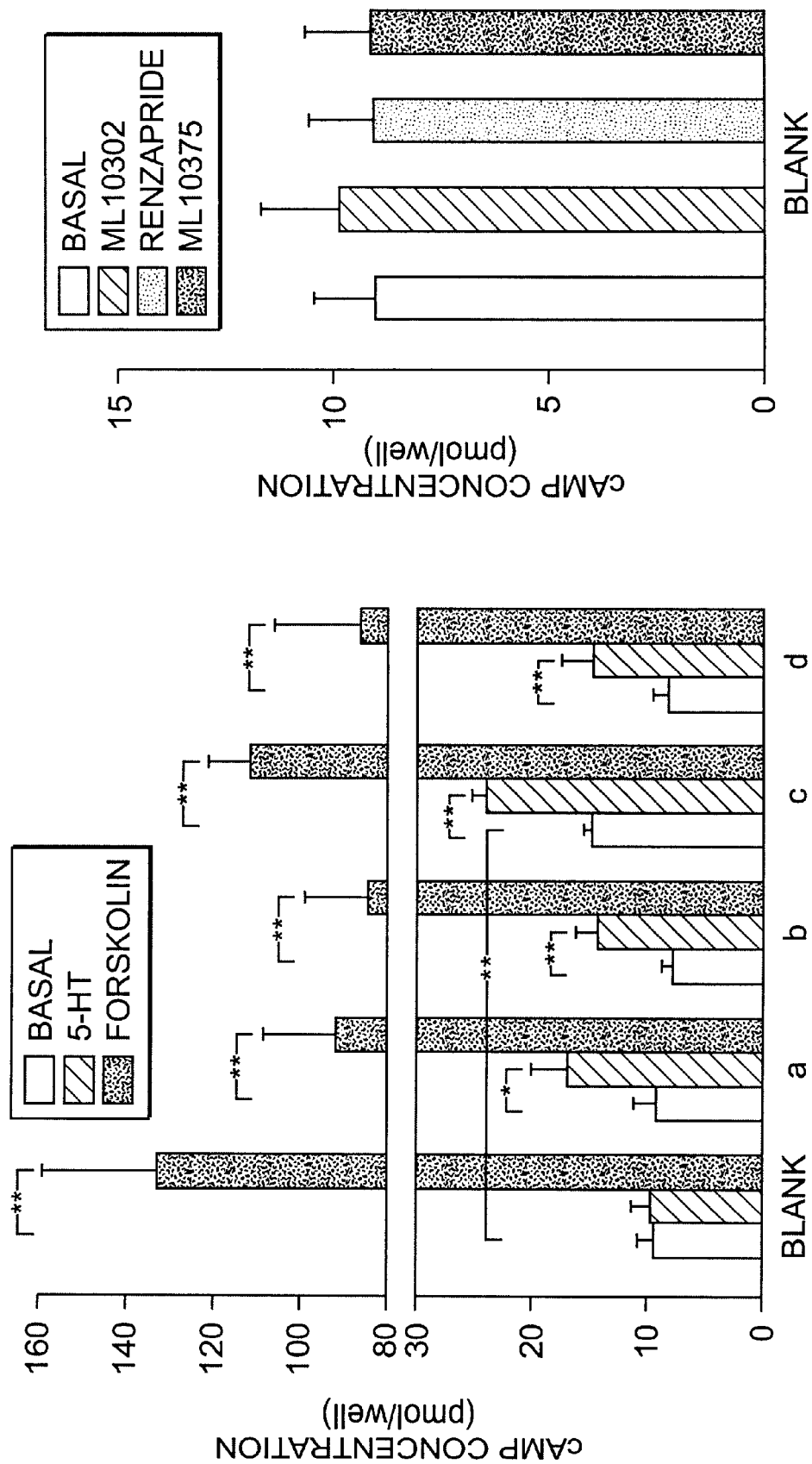

To examine and compare the capacity of the 5-HT$_4$ receptors to be coupled to adenylate cyclase, cAMP synthesis was assayed in the COS-7 cells transiently transfected with the 5-HT$_{4(a)}$, 5-HT$_{4(b)}$, 5-HT$_{4(c)}$ and 5-HT$_{4(d)}$ cDNAs. The basal cAMP values were not significantly different in the "blank"-transfected cells and the cells expressing the receptors 5-HT$_{4(a)}$, 5-HT$_{4(b)}$ and 5-HT$_{4(d)}$, indicating that these expressed isoforms of the receptor had no intrinsic activity, regarding cAMP formation, in transiently transfected cells in the absence of agonists (FIG. 5a). However, the transient expression of the 5-HT$_{4(c)}$ isoform led to a significant increase in the basal activity level of adenylate cyclase in the absence of agonists 5-HT$_4$ (FIG. 5a). The latter result indicates that the expression of 5-HT$_{4(c)}$ in the system described generates a spontaneously active receptor state. 5-HT (1 $\mu$M) has no effect on the basal activity of adenylate cyclase in the "blank"-transfected COS-7 cells (FIG. 5a), indicating that the endogenous adenylate cyclase-coupled serotoninergic receptors are not present in these cells. In the cells expressing 5-HT$_{4(a)}$, 5-HT$_{4(b)}$, 5-HT$_{4(c)}$ and 5-HT$_{4(d)}$ the addition of 5-HT (1 $\mu$M) significantly increases the cAMP concentration by 82%, 85%, 64% and 77% respectively (FIG. 5a). Forskolin (10 $\mu$M), which is a direct activator of adenylate cyclase, induces similar increases in cAMP concentrations in the cells expressing the isoforms of the receptor 5-HT$_4$ and in the "blank"-transfected COS-7 cells (FIG. 5A), indicating that the maximum activation potential of the adenylate cyclase has not been affected in the cells expressing the receptors 5-HT$_4$. The receptor 5-HT$_4$ agonists ML10302 and renzapride and the receptor 5-HT$_4$ antagonist ML10375 have no significant effect on the basal cAMP levels in the "blank"-transfected COS-7 cells (FIG. 5B). In the cells expressing the isoforms of the receptor 5-HT$_4$, ML10302 behaves as a weak 5-HT$_4$ agonist, and shows only 28 to 34% of the stimulatory effect of 5-HT (FIG. 5C), despite a high affinity for the receptor (Table 1). In addition, the preincubation of the cells with 1 $\mu$M ML10302, prior to the addition of 5-HT (1 $\mu$M), significantly antagonizes the capacity of 5-HT to increase basal cAMP levels (FIG. 5C). As described by Blondel et al. (1997), renzapride also behaves like a weak 5-HT$_4$ agonist in the cells expressing the receptor isoform 5-HT$_{4(a)}$, and increases cAMP formation by only 56% in the cells (FIG. 5D), despite an affinity for the receptor 5-HT$_{4(a)}$ which is similar to that of 5-HT (Table 1). However, renzapride behaves like a total agonist in the cells expressing the 5-HT$_{4(b)}$, 5-HT$_{4(c)}$ and 5-HT$_{4(d)}$ isoforms, in that the renzapride-induced cAMP formation mediated by these splicing variants of the receptor is not significantly different from the 5-HT-induced cAMP formation (FIG. 5D). The 5-HT$_4$ antagonist ML10375 (Yang et al., 1997), at a concentration of 1 $\mu$M, had no significant effect on the basal cAMP levels in the cells expressing the receptor isoforms 5-HT$_{4(a)}$ and 5-HT$_{4(b)}$, but significantly reduced the basal cAMP levels in the cells expressing the receptor isoforms 5-HT$_{4(c)}$ and 5-HT$_{4(d)}$ (by 21% and 24% respectively, FIG. 5E). In addition, the preincubation of-t:he cells expressing the receptor 5-HT$_4$ isoforms with 1 $\mu$M ML10375, prior to the addition of 5-HT (1 $\mu$M), antagonizes the capacity of 5-HT to significantly increase the basal cAMP levels (FIG. 5E).

TABLE 1

Comparison of the binding affinities of diverse receptor 5-HT$_4$ agonists and antagonists on the receptors 5-HT$_{4(a)}$, 5-HT$_{4(b)}$, 5-HT$_{4(c)}$ and 5-HT$_{4(d)}$

| | K$_i$ (nM) | | | |
|---|---|---|---|---|
| | 5-HT$_{4(a)}$ | 5-HT$_{4(b)}$ | 5-HT$_{4(c)}$ | 5-HT$_{4(d)}$ |
| 5-HT | 772 ± 278 | 1151 ± 170 | 481.9 ± 112 | 330 ± 113 |
| 5-MeOT | 2080 ± 508 | 2443 ± 510 | 1020 ± 236 | 553 ± 149 |
| ML10302 | 8.4 ± 1.5 | 10.72 ± 2.9 | 7.98 ± 2.77 | 3.69 ± 1.25 |
| BIMU1 | 373 ± 119 | 123.4 ± 9.0 | 66 ± 8.37 | 38.85 ± 12 |
| Renzapride | 635 ± 148 | 1179 ± 142 | 636 ± 91 | 173 ± 40 |
| Zacopride | 7750 ± 1615 | 11490 ± 950 | 10630 ± 2160 | 3599 ± 1835 |
| GR113808 | 0.33 ± 0.033 | 0.53 ± 0.10 | 0.41 ± 0.13 | 0.078 ± 0.24 |
| ML10375 | 0.56 ± 0.11 | 1.62 ± 0.82 | 0.61 ± 0.08 | 0.41 ± 0.10 |

The experiments correspond to the competition of various compounds for [$^3$H]GR113808 binding to membranes of transiently transfected COS-7 cells. For each isoform of the human receptor 5-HT$_4$, the [$^3$H]GR113808 concentration was adjusted to 50% of the K$_d$ value. The estimations of affinity are given as K$_i$ values in nM, and are determined from IC$_{50}$ values obtained by computer-assisted nonlinear curve analysis (GraphPad, Prism Software). The K$_i$ values are representative of at least two determinations. The order of potencies of the drugs tested is identical for the four 5-HT$_4$ isoforms, and is: GR113808>ML10375>ML10302>BIMUL>Renzapride=5-HT>5-MeOT>Zacopride.

EXAMPLE 5

ML10375: Reverse Agonist of the Receptor 5-HT$_4$

Figure 6B:
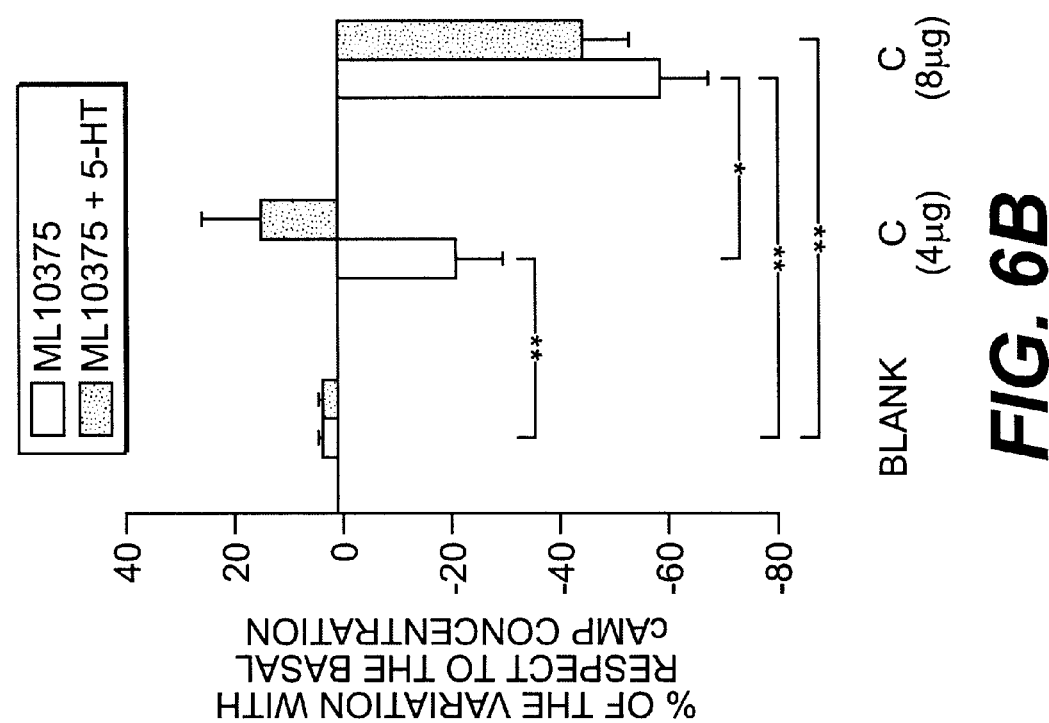
Figure 6A:
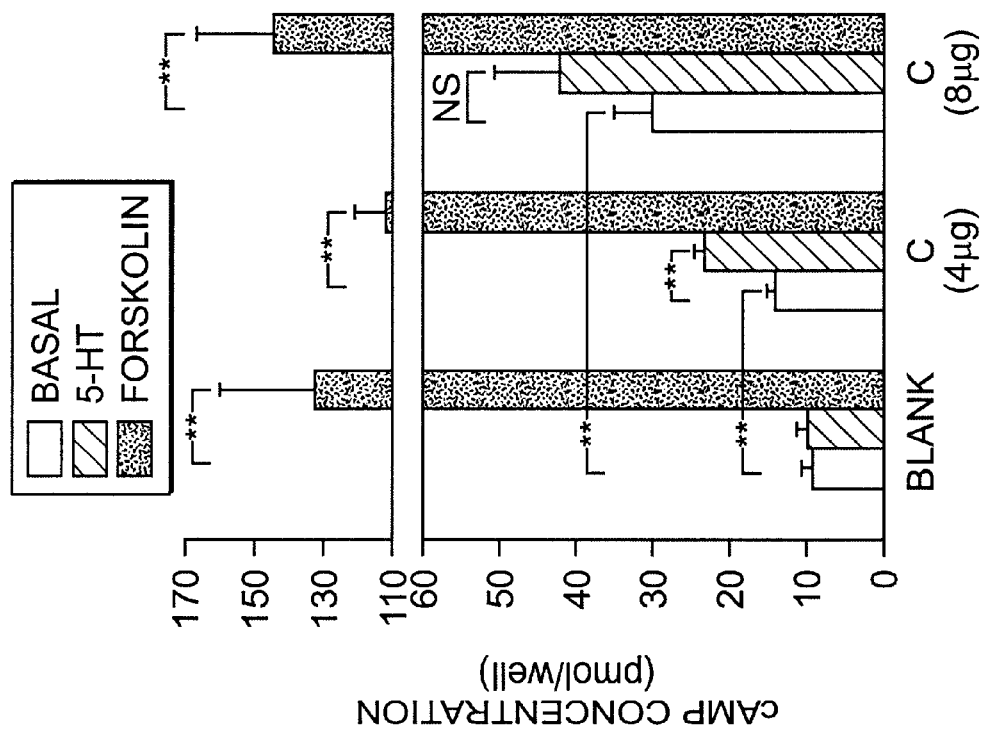

ML10375 is capable of reducing the cAMP levels in the cells expressing the 5-HT$_{4(c)}$ and 5-HT$_{4(d)}$ isoforms in the absence of any stimulation of the receptor by 5-HT$_4$ agonists. To test the hypothesis that ML10375 may constitute a reverse agonist for the human receptor 5-HT$_4$, the 5-HT$_{4(c)}$ isoform was overexpressed in COS-7 cells in order to increase the frequency of the spontaneously active state of the receptor. The COS-7 cells were transfected with 4 to 8 μg of plasmid DNA per well in order to obtain an increase in the expression levels of the receptor 5-HT$_{4(c)}$. The transfection of the COS-7 cells using 4 μg and 8 μg of plasmid DNA increased the basal cAMP level by 59% and by 235% respectively (FIG. 6A). 5-HT (1 μM) induced an increase of 64% in the basal cAMP level in the cells transfected with 4 μg of plasmid DNA, but did not significantly increase the basal cAMP level in the cells transfected with 8 μg of plasmid DNA (FIG. 6A). The latter result indicates that in the cells overexpressing the receptor isoform 5-HT$_{4(c)}$, the frequency of the spontaneously active receptor prevents the stimulatory effect of the 5-HT on adenylate cyclase activity. Forskolin (10 μM) induced similar increases in cAMP concentrations in the cells transfected with either 4 μg or 8 μg of plasmid DNA and in the "blank"-transfected cells (FIG. 6A), indicating that the maximum activation potential of adenylate cyclase was not affected in the cells overexpressing the 5-HT$_{4(c)}$ isoform. In the COS-7 cells transfected with 4 μg and 8 μg of plasmid DNA, ML10375 (1 μM) decreased the basal cAMP values by 24% and 62% respectively (FIG. 6B). In the cells transfected with 4 μg of plasmid DNA, the preincubation with ML10375 (1 μM) antagonized the stimulatory effect of 5-HT (1 μM) on the basal cAMP (FIG. 6B). In the cells transfected with 8 μg of plasmid DNA, the preincubation with ML10375 (1 μM) induced a decrease of 47% in the basal cAMP level, even in the presence of 1 μM 5-HT. (FIG. 6B).

Figures 6C, 6D:
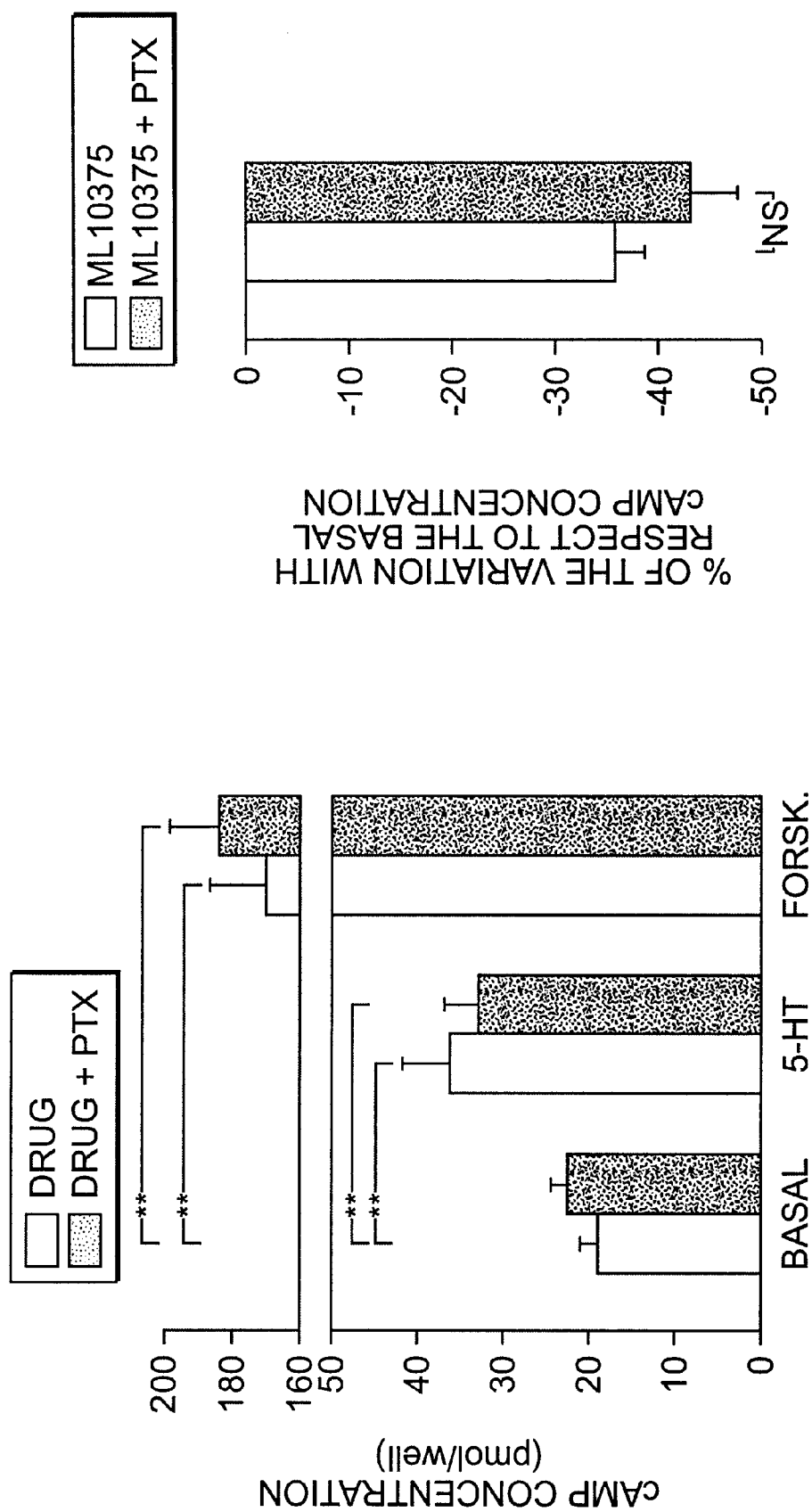

To test whether the effect of ML10375 on the cAMP level corresponds to an activation of the spontaneously active receptors 5-HT$_{4(c)}$ or to an inhibition of adenylate cyclase activity via the Gi protein-mediated regulatory pathway, the effect of ML10375 was examined in the COS-7 cells transfected with 6 pg of 5-HT$_{4(c)}$ plasmid DNA, in the presence or absence of PTX (100 ng/ml). The PTX treatment modified neither the basal cAMP level nor the 5-HT-induced and forskolin-induced stimulation of cAMP in the transfected cells (FIG. 6C). In addition, the PTX treatment did not significantly modify the ML10375-induced reduction in basal cAMP in the transfected cells (FIG. 6D).

EXAMPLE 6

Pharmacological Characterization of the Receptor 5-HT$_4$ Splicing Variants Stably Expressed in CHO Cells Materials:

HAM-F12 medium was obtained from Gibco-BRL. ML 10375 (2-(cis-3,5-dimethylpiperidino)ethyl 4-amino-5-chloro-2-methoxybenzoate) was synthesized according to Langlois et al., 1994; Yang et al., 1997. GR113808 (([1-[2-(methylsulphonyl)]amino]ethyl]-4-piperidyl)-methyl 1-methyl-1H-indole-3-carboxylate) was obtained from the Glaxo Research Group (Ware, Hertfordshire, U.K.) and [$^3$H]GR113808 was obtained from Amersham (Arlington Heights, Ill.). The electroporator used was a Gene Pulser obtained from Biorad.

1. DNA Transfection

The entire coding region of the 5-HT$_{4(c)}$ and 5-HT$_{4(d)}$ cDNAs was subcloned into a mammalian expression vector pRC/CMV (Invitrogen, Carlsbad, Calif.). The CHO cells are stably transfected by electroporation (250 V, 960 μF) with the plasmid PRc/CMV, containing the clone h5-HT$_{4(c)}$ or h5-HT$_{4(d)}$, cleaved with the restriction enzyme Kpn1 (10 μg of plasmid for 10$^7$ cells). The cells are cultured in HAM-F12 medium supplemented with 10% of heat-inactivated foetal calf serum. After 48 hours, geneticin (1.25 mg/ml) is added to the medium. Twelve days later, the clones are individualized and cultured in 12-well plates. Clone selection is carried out by studying the stimulation of the cAMP formed in the presence of 1 μM serotonin. For the radioligand binding assays or for the measurement of cAMP formation, the cells transfected with the receptor 5-HT$_4$ cDNA constructs were compared with the "blank"-transfected cells, which were exposed to the unmodified pRC/CMV plasmid.

2. Membrane Preparation

Each flask of cells intended for the radioligand binding assays was washed twice with a phosphate buffer (PBS). The cells were then scraped, collected and centrifuged at 300 g for five minutes. The pellet was resuspended in 2.5 ml of ice-cold HEPES buffer (50 mM, pH 7.4) and homogenized with an Ultraturax tissue grinder. The lysate was then centrifuged at 40,000 g for 20 minutes at 4° C. The resulting pellet was resuspended in 15 volumes of HEPES buffer (50 mM, pH 7.4). The membrane preparations were maintained in ice and used within two hours for radioligand binding assays. The protein concentrations were determined by the method of Lowry et al., 1951, using bovine serum albumin as standard.

3. Radioligand Binding Assays

The radioligand binding studies were carried out in 500 µl of buffer (50 mM HEPES, pH 7.4) [lacuna] 20 µl of ML 10375, to give a final concentration of 10 µM, (for determining the nonspecific binding), or of a buffer (for determining total binding), and 20 µl of [$^3$H]GR113808 to give a final concentration of 50% of $K_d$ and 50 µl (100 to 200 µg) of membrane preparation. The saturation studies were performed using [$^3$H]GR113808 at 9 different concentrations ranging from 0.01 to 3.5 nM. The tubes were incubated at 25° C. for 30 minutes. The reaction was stopped by rapid filtration, under vacuum, through Whatman GF/B filter paper using the Brandel 48R cell harvester. The filters were presoaked in a solution of PEI (0.1%) to reduce the binding to the filters. The filters were then washed with an ice-cold buffer (50 mM Tris-HCl, pH 7.4) and placed in 4 ml of "ready safe" scintillation cocktail (Beckman, Fullerton, Calif.) overnight. The radioactivity was measured using a Beckman LS 6500 C liquid scintillation counter. The binding data were analysed by computer-assisted nonlinear regression analysis (Graph Pad Prism Program, Graph Pad Software, Increase., San Diego, Calif.).

4. Results of the Binding Assays

The saturation analysis using [$^3$H]GR113808 revealed unique high affinity sites which can be saturated for the two splicing variants of the receptor (FIG. 7). Similar $K_d$ values for [$^3$H]GR113808 were found between the two isoforms (5-HT$_{4(c)}$, 0.42±0.04 nM; 5-HT$_{4(d)}$, 0.23±0.03 nM). The density of the receptors expressed in the CHO cells ($B_{max}$) is 568.1±17.4 fmol/mg of protein for 5-HT$_{4(c)}$ and 179.9±5.8 fmol/mg of protein for 5-HT$_{4(d)}$. The nonspecific binding increases in nonlinear fashion with the increase in ligand concentration (FIG. 7).

EXAMPLE 7

Stimulation of cAMP Production by the 5-HT$_4$ Splicing Variants Stably Expressed in CHO Cells Materials:

DMEM and HAM-F12 media were obtained from GIBCO-BRL. 5-Hydroxytryptamine (5-HT) was obtained from Aldrich (L'Isle d'Abeau Chesnes, France) and all the other drugs were obtained from Sigma (L'Isle d'Abeau Chesnes, France).

1. Measurement of cAMP Formation

To measure intracellular cAMP accumulation, the stably transfected CHO cells were incubated in the HAM-F12 medium containing 5 mM theophylline, 10 mM HEPES and 10 µM pargyline, for 15 minutes at 37° C. in the presence of 5% $CO_2$. 5-HT (1 µm) was added, and the cells were incubated for a further 15 minutes at 37° C. in the presence of 5% $CO_2$. The reaction was stopped by aspiration of the medium and addition of 500 µl of ice-cold ethanol. After one hour at room temperature, the cells were scraped, and everything was collected and freeze-dried. The pellet was resuspended in 350 µl of PBS and centrifuged for 5 min at 300 g. The cAMP was quantified in the supernatant using a radio-immunological assay (E.R.I.A. assay kit from Immunotech, Marseilles). Student's t tests were carried out using the program Quick TEst.

2. Stimulation of cAMP Production.

To examine and compare the capacity of the 5-HT$_4$ receptors to be coupled to adenylate cyclase, cAMP synthesis was assayed in the CHO cells stably transfected with the h5-HT$_{4(c)}$ and h5-HT$_{4(d)}$ cDNAs. The basal cAMP values were higher in the cells expressing the receptors h5-HT$_{4(c)}$ (9.8±1.6 pmol/well) and h5-HT$_{4(d)}$(12.1±0.9 pmol/well) then in the "blank"-transfected cells (3.6±0.4 pmol/well), indicating that these expressed isoforms of the receptor possess an intrinsic activity, regarding cAMP formation, in stably transfected cells, in the absence of agonists. In the cells expressing h5-HT$_{4(c)}$ and h5-HT$_{4(d)}$, the addition of 5-HT (1 µM) significantly increases the cAMP concentration (by 91% for h5-HT$_{4(c)}$ and by 118% for h5-HT$_{4(d)}$ respectively, FIG. 8), whereas 5-HT has no effect on the "blank"-transfected CHO cells (FIG. 8).

EXAMPLE 8

Production of Rabbit Polyclonal Antibodies Against Synthetic Peptides Derived from the Sequences of the Receptor h5-HT$_4$ Isoforms.

The table below presents the sequence of the synthetic peptides prepared from the receptor 5HT$_4$ isoforms:

| SEQ ID | Peptide designation | Sequence | Corresponding domain |
|---|---|---|---|
| 5 | F26V | FGAIELVQDIWIYGEVFCLVRTSLDV | extracellular loop I |
| 6 | G21V | GIICLIEKRKFNQNSNSTYCV | extracellular loop II |
| 7 | C24T | CGQWESQBHPPATSPLVAAQPSDT | C-terminal portion isoform a |
| 8 | Y23F | YGHHQELEKLPIHNDPESLESCF | C-terminal portion isoform b |
| 9 | C21S | CGTETDRRNFGIRKRRLTKPS | C-terminal portion isoform c |

-continued

| SEQ ID | Peptide designation | Sequence | Corresponding domain |
|---|---|---|---|
| 10 | C7F | C-Ahx-THVLRF | C-terminal portion isoform d |

Ahx = aminohexanoic acid

Rabbits were immunized with 250 µg of the peptides F26V and G21V, which correspond to the first and the second extracellular loop of the receptor h5-T$_4$, and with 250 µg of peptides C24T and C21S, which correspond respectively to the C-terminal portion of the h5-HT$_{4(a)}$ and h5-HT$_4$ (c) isoforms. These peptides where injected in their original state in the presence of 3 mg of methylated bovine serum albumin and 1 ml of complete Freund's adjuvant. After three weeks, the rabbits received the same immunogens in the presence of incomplete Freund's adjuvant, followed by the same immunization one month later. The antisera were sampled one week after the final injection.

The peptides Y23F, which corresponds to the C-terminal portion of the h5-HT$_{4(b)}$ isoform, and C7F, which corresponds to the C-terminal portion of the h5-T$_{4(d)}$ isoform, were coupled to bromoacetylated serum albumin, before immunization with 2.3 µmol of peptide coupled to 3.4 mg of modified bovine serum albumin. The first immunization, in complete Freund's adjuvant, is followed by two other injections in incomplete Freund's adjuvant as described in the previous paragraph. The antisera were sampled one week after the final injection.

FIG. 9 gives the optical density values of an immunoenzymatic assay of ELISA type on the respective peptides adsorbed (5 µg/ml in a carbonate buffer at pH=9.5) onto MAXIsorb plates (Nunc, Denmark). The antisera were incubated for one hour at 37° C., and revealed with a peroxidase-coupled goat anti-rabbit IgG antibody conjugate (dilution 1/10,000) and the substrate H$_2$O$_2$-ABTS.

EXAMPLE 9

Demonstration, Using the Anti-G21V Antibody, of the Presence of the Receptor 5-HT$_{4(c)}$ in the Stably Transfected CHO Cells The presence of the receptor 5-HT$_{4(c)}$ in the CHO cells stably expressing this isoform of the receptor was demonstrated by Western blot using the common G21V antibody developed in the context of this study. [lacuna] the 5HT$_{4(a)}$ (FIG. 10, line 2) and 5-HT$_{4(c)}$ (FIG. 10, line 3) isoforms. The CHO cells were transfected with the expression vector encoding the form (c) of the receptor 5-HT$_4$, and were selected for their neomycin resistance. For comparison, other CHO cells were transfected with the expression vector encoding the form (a) of the receptor 5-HT$_4$. Fifty µg of proteins originating from membrane extracts are separated on a 10% polyacrylamide gel, and then transferred onto nitrocellulose membrane. After a 16-h incubation in the presence of 60 µg of anti-5-HT$_4$ (G21V) antibodies, the blot is revealed by chemiluminescence (ECL, Amersham, Arlington Heights, Ill.) and scanned. Line 1 of FIG. 10 indicates the result obtained on the control CHO cells, in which no labelling was detected; lines 2 and 3 come from clones of CHO cells overexpressing respectively the receptors 5-HT$_{4(a)}$ and 5-HT$_{4(c)}$. A band which migrates approximately with the size of 60 kDa is visualized.

EXAMPLE 10

Demonstration, using the anti-C21S and anti-C7F antibodies, of the presence respectively of the receptors h5-HT$_{4(c)}$ and h5-HT$_{4(d)}$ in the stably transfected CHO cells Using antibodies directed against the C-terminal sequence specific for the receptor h5-HT$_{4(c)}$ (anti-C21S) and for the receptor h5-HT$_{4(d)}$ (anti-C7F), the presence of these respective receptors on homogenates of cells expressing the two isoforms could be demonstrated. The specificity of the protein bands recognized was determined by the extinction of the response on immunoblot in the presence of inhibiting peptides (FIG. 11a and 11k, second lines). The h5-HT$_{4(c)}$ isoform is recognized in its glycosylated and nonglycosylated form (corresponding to molecular weights of 60 and 44 kDa); the h5-HT$_{4(d)}$ isoform is recognized in its nonglycosylated form (corresponding to a molecular weight of 40 kDa) (FIG. 11a and 11b, first lines).

REFERENCES

Adham N., Gerald C., Schechter L., Vaysse P., Weinshank R., and Branchek T. (1996). [3H]5-hydroxy-tryptamine labels the agonist high affinity state of the cloned rat 5-HT4 receptor. Eur. J. Pharmacol. 304, 231–235.

Ansanay H., Sebben M., Bockaert J., and Dumuis A., (1996). Pharmacological comparison between [3H] GR113808 binding sites and functional 5-HT4 receptors in neurons. Eur. J. Pharmacol. 298, 165–174.

Benoit et al., PNAS USA, (1982), 79, 917–921.

Blondel O., Vandecasteele G., Gastineau M., Leclerc S., Dahmoune Y., Langlois M., and Fischmeister R. (1997). Molecular and functional characterization of a 5-HT4 receptor cloned from human atrium. FEBS Lett. 412, 465–474.

Bonhomme N., De Deurwaerdere P., Le Moal M., and Spampinato U. (1995). Evidence for S-HT4 receptor subtype involvement in the enhancement of striatal dopamine release induced by serotonin: a microdialysis study in the halotane-anesthetized rat. Neuropharmacology 34, 269–279.

Boussif O., Lezoualc'h F., Zanta M. A., Mergny M. D., Scherman D., Demeneix B., and Behr J. P. (1995). A versatile vector for gene and oligonucleotide transfer into cells in culture and in vivo: polyethyleneimine. Proc. Natl. Acad. Sci. USA 92, 7297–7301.

Candura S. M., Messori E., Franceschetti G. P., D'Agostino G., Vicini D., Tagliani M., and Tonini M. (1996). Neural 5-HT4 receptors in the human isolated detrusor muscle: effects of indole, benzimidazolone and substituted benzamide agonists and antagonists. Br. J. Pharmacol. 118, 1965–1970.

Claeysen S., Faye P., Sebben M., Lemaire S. Bockaert J., and Dumuis A. (1997). Cloning and expression of human 5-HT4s receptors. Effect of receptor density on their coupling to adenylyl cyclase. FEBS Letters 398, 19–25.

Claeysen S., Sebben M., Journot L., Bockaert J., and Dumuis A. (1996). Cloning, expression and pharmacology of the mouse 5-HT4L receptor. FEBS Letters 398, 19–25.

Coughlin, S. R. (1994). Expanding horizons for receptors coupled to G proteins: diversity and disease. Curr. Opin. Biol. 6, 191–197.

Dohlman H. G., Thorner J., Caron M. G., and Lefkowitz R. J. (1991). Model systems for the study of seven-transmembrane-segment receptors. Annu. Rev. Biochem. 60, 653–88.

Eglen R. M., Wong E. H. F., Dumuis A., and Bockaert J. (1995). Central 5-HT4 receptors. Trends Pharmacol. Sci. 16, 391–397.

Ford A. P. and Clarke D. E. (1993). The 5-HT4 receptor. Med. Res. Rev. 13, 633–662.

Freedman N. J., Liggett S. B., Drachman D. E., Pei G., Caron M. G., and Lefkowitz R. J. (1995). Phosphorylation and desensitization of the human β1-adrenergic receptor. J. Biol. Chem. 270, 17953–17961.

Gerald C., Adham N., Kao H. T., Olsen M. A., Laz T. M., Schechter L. E., Bard J. E., Vaysse P. J. J., Hartig P. R., Branchek T. A., and Weinshank R. L. (1995). The 5-HT4 receptor: molecular cloning and pharmacological characterization of two splice variants. EMBO J. 14, 2806–2815.

Hedge S. and Eglen R. (1996). Peripheral 5-HT4 receptors. FASEB J. 10, 1398–1407.

Heidmann D. E. A., Metcalf M. A., Kohen R., and Hamblin M. W. (1997). Four 5-hydroxytryptamine7 (5-HT7) receptor isoforms in human and rat produced by alternative splicing: species differences due to altered intron-exon organization. J. Neurochem. 68, 1372–1381.

Hoyer D., Clarke D. E., Fozard J. R., Hartig P. R., Martin G. R., Mylecharane E. J., Saxena P. R. and Humphrey P. P. A. (1994). International Union of Pharmacology classification of receptors for 5-hydroxytryptamine (Serotonin). Pharmacol. Rev. 46, 157–204.

Hoyer D. and Martin G. (1997). 5-HT receptor classification and nomenclature: towards a harmonization with the human genome. Neuropharmacology 36, 419–428.

Kaumann A. J. (1994). Do human atrial 5-HT4 receptors mediate arrhythmias? Trends Pharmacol. Sci. 15, 451–455.

Kaumann A. J., Lynham J. A., and Brown A. M. (1996). Comparison of the densities of 5-HT4 receptors, β1- and β2-adrenoceptors in human atrium: functional implications. Naunyn-Schmied. Arch. Pharmacol. 353, 592–595.

Kaumann A. J., Lynham J. A., and Brown A. M. (1995). Labelling with [125]-SB 207710 of a small 5-HT4 receptor population in piglet right atrium: functional relevance, Br. J. Pharmacol. 115, 933–936.

Kaumann A. J., Sanders L., Brown A. M., Murray K. J., and Brown M. J. (1991). A 5-HT4-like receptor in human right atrium. Naunyn-Schmied. Arch. Pharmacol. 344, 150–157.

Kenakin T. (1996). The classification of seven transmembrane receptors in recombinant expression systems. Pharmacol. Rev. 48, 413–463.

Köhler and Milstein (1975). Nature Vol. 256, pp. 495–497.

Langlois M., Zhang L., Yang D., Brémont B., Shen S., Mahara L., and Croci T. (1994). Design of a potent 5-HT4 receptor agonist with nanomolar affinity. Biomed. Chem. Lett. 4, 1433–1436.

Lowry O. H., Rosebrough N. J., Farr A. L., and Randall R. J. (1951). Protein measurements with the folin reagent. J. Biol. Chem. 193, 265–275.

Marchetti-Gauthier E., Roman F. S., Dumuis A., Bockaert J., and Soumireu-Mourat B. (1997). BIMU1 increases associative memory in rats by activating 5-HT4 receptors. Neuropharmacology 36, 697–706.

Namba T., Sugimoto Y., Negishi M., Irie A., Ushikubi F., Kakizuka A., Ito S., Ichikawa A., and Narumiya S. (1993). Alternative splicing of C-terminal tail of prostaglandin E receptor subtype EP3 determines G-protein specificity. Nature 365, 166–170.

Newton C. R. and Graham A. (1994). Isolation and construction of DNA clones, in PCR (Graham J. M. and Billington D., eds.), pp. 47–57, Bios Scientific Publishers, Oxford, UK.

Pei G., Samama P., Lohse M., Wang M., Codina J., and Lefkowitz R. (1994). A constitutively active mutant P2-adrenergic receptor is constitutively desensitized and phosphorylated. Proc. Natl., Acad. Sci. USA 91, 2699–2702.

Prezeau L., Gomeza J., Ahern S., Mary S., Galvez T., Bockaert J., and Pin J. P. (1996). Changes in the carboxy-terminal domain of metabotropic glutamate receptor 1 by alternative splicing generate receptors with different agonist-independent activity. Mol. Pharmacol. 49, 422–429.

Reynolds G. P., Mason L., Meldrum A., De Keczer S., Parnes H., and Wong E. H. F. (1995). 5-hydroxytryptamine (5-HT)4 receptors in post mortem human brain tissue: distribution, pharmacology and effects of neurodegenerative diseases. Br. J. Pharmacol. 114, 993–998.

Ronde P., Ansanay H., Dumuis A., Miller R., and Bockaert J. (1995). Homologous desensitization of 5-hydroxytryptamine4 receptors in rat oesophagus: functional and second-messenger studies. J. Pharmacol. Exp. Ther. 272, 977–983.

Saxena P. R. (1995). Serotonin receptors: subtypes, functional responses and therapeutic relevance. Pharmacol. Ther. 66, 339–368.

Spengler D., Waeber C., Pantaloni C., Holsboer F., Bockaert J., Seeburg P. H., and Journot L. (1993). Differential signal transduction by five splice variants of the PACAP receptor. Nature 365, 170–175.

Ullmer C., Schmuck K., Kalkman H. O., and Lübbert H. (1995). Expression of serotonin receptor mRNAs in blood vessels. FEBS Lett. 370, 215–221.

Van den Wyngaert I., Gommeren W., Verhasselt P., Jurzak M., Leysen J., Luyten W., Bender E. (1997). Cloning and expression of a human serotonin 5-HT4 receptor cDNA. J. Neurochem. 69, 1810–1819.

Waeber C., Sebben M., Grossman C., Javoy-Agid F., Bockaert J., and Dumuis A. (1993). [3H]-GR113808 labels 5-HT4 receptors in the human and guinea-pig brain. Neuroreport 4, 1239–1242.

Westphal R. S., Backstrom J. R., and Sander-Bush E. (1995). Increased basal phosphorylation of the constitutively active serotonin 2C receptor accompanies agonist-mediated desensitization. Mol. Pharmacol. 48, 200–205.

Wong E. H., Reynolds G. P., Bonhaus D. W., Hsu S., and Eglen R. M. (1996). Characterization of [3H]GR113808 binding to 5-HT4 receptors in brain tissues from patients with neurodegenerative disorders. Behav. Brain Res. 73, 249–252.

Yang D., Soulier J. L., Sicsic S., Mathe-Allainmat M., Bremont B., Croci T., Cardamore R. Aureggi G., and Langlois M. (1997). New esters of 4-amino-5-chloro-2-methoxybenzoic acid as potent agonists and antagonists for 5-HT4 receptors. J. Med. Chem. 40, 608–621.

What is claimed is:

1. Isolated nucleotide sequence chosen from the sequence SEQ ID No. 1, the sequence SEQ ID No. 3, the nucleotide sequences derived from the sequence SEQ ID No. 1 or from the sequence SEQ ID No. 3 due to the degeneracy of the genetic code, to mutation, to deletion or to insertion, and the nucleotide sequences which are capable of specifically hybridizing with the sequence SEQ ID No. 1 or the sequence SEQ ID No. 3.

2. Cloning and/or expression vector containing a nucleotide sequence according to claim 1.

3. Host cell transformed with a vector according to claim 2.

4. Method for producing a biologically active recombinant polypeptide 5-HT$_{4(c)}$ or 5-HT$_{4(d)}$, fragment or derivative of this polypeptide, in which cells transformed according to claim 3 are cultured under conditions which allow the expression of a polypeptide of sequence SEQ ID No. 2 or SEQ ID No. 4, or any biologically active fragment or derivative of this polypeptide, and said biologically active polypeptide, fragment or derivative of this polypeptide is recovered.

5. A method for evaluating the pharmacological properties of the compounds which are capable of binding to the polypeptide 5-HT$_{4(d)}$, termed receptor 5-HT$_{4(d)}$ ligands, comprising the steps of:
   a) culturing host cells according to claim 3 which express the polypeptide 5-HT$_{4(d)}$ ligand; and
   b) evaluating the capacity of the ligand for modifying signal transduction.

6. The method according to claim 5 in which the capacity of the ligand for modulating signal transduction is evaluated by determining the intracellular cAMP concentration or adenylate cyclase activity.

* * * * *